US006987089B1

(12) United States Patent  
Choi et al.

(10) Patent No.: US 6,987,089 B1  
(45) Date of Patent: Jan. 17, 2006

(54) MOUSE CIA PROTEIN AND CIA GENE HAVING ANTI-APOPTOTIC ACTIVITY AS A SELECTIVE INHIBITOR OF CAD INTERACTING ASK1 USE THEREOF

(75) Inventors: Eui-Ju Choi, #501-605 Wooseong 5cha Apt., Dogok 2-dong, Kangnam-ku, Seoul (KR) 135-272; Ssang-Gu Cho, Seoul (KR); Yong Hee Lee, Seoul (KR); Jin Woo Kim, Seoul (KR); Sung Wook Chi, Kyongki-do (KR)

(73) Assignee: Eui-Ju Choi, Seoul (KR)

( * ) Notice: Subject to any disclaimer, the term of this patent is extended or adjusted under 35 U.S.C. 154(b) by 338 days.

(21) Appl. No.: 10/296,655

(22) PCT Filed: Jun. 26, 2000

(86) PCT No.: PCT/KR00/00667

§ 371 (c)(1),  
(2), (4) Date: Nov. 26, 2002

(87) PCT Pub. No.: WO01/96550

PCT Pub. Date: Dec. 20, 2001

(51) Int. Cl.  
*A01N 37/18* (2006.01)  
*A61K 38/00* (2006.01)

(52) U.S. Cl. .......................................... 514/2; 514/12
(58) Field of Classification Search .................. 514/2  
See application file for complete search history.

(56) References Cited

U.S. PATENT DOCUMENTS

| | | | |
|---|---|---|---|
| 6,525,174 B1 * | 2/2003 | Young et al. ............... 530/350 |
| 2002/0077270 A1 * | 6/2002 | Rosen et al. ................... 514/1 |
| 2003/0065160 A1 * | 4/2003 | Young et al. ............. 536/23.2 |
| 2003/0092893 A1 * | 5/2003 | Young et al. ............ 530/388.1 |
| 2003/0181692 A1 * | 9/2003 | Ni et al. .................... 536/23.1 |
| 2003/0228584 A1 * | 12/2003 | Tang et al. ..................... 435/6 |
| 2004/0034208 A1 * | 2/2004 | Tang et al. ................ 536/23.2 |

FOREIGN PATENT DOCUMENTS

WO  WO 02/000677  * 6/2001

OTHER PUBLICATIONS

Mayer et al. Sequence and analysis of chromosome 4 of the plant *Arabidopsis thaliana*. Nature. 1999. vol. 204, pp. 769-777.*

Parsons, J.A. Peptide Hormones. Jun. 1976. Biological Council. The Co-ordinating Commitee for Sypomsia on Drug Action. pp. A0 and 1-7.*

Chen, Zhihong et al., "ASK1 mediates apoptotic cell death induced by genotoxic stress", Oncogene, Jan. 1999, 18(1), pp. 173-180.

Takeda, Kohsuke et al, "Apoptosis Signal-regulating Kinase 1 (ASK1) Induces Neuronal Differentiation and Survival of PC12 Cells", The Journal of Biological Chemistry, Mar. 31, 2000, 275(13), pp. 9805-9813.

* cited by examiner

*Primary Examiner*—Christopher R Tate  
*Assistant Examiner*—Marcela M Cordero Garcia  
(74) *Attorney, Agent, or Firm*—Gates & Cooper LLP

(57) ABSTRACT

The present invention relates to novel mouse CIA protein and CIA gene having anti-apoptotic activity isolated by yeast 2-hybrid screening which inhibit apoptosis mediated by caspase activated-DNase, CAD and apoptosis signal-regulating kinase 1, ASK1. Since mouse CIA protein and CIA gene of the present invention inhibit apoptotic cell death and DNA fragmentation by selectively interacting with CAD and ASK1 as a negative regulator, CIA protein is useful for an effective inhibitor of CAD and ASK1 protein or a cure of various diseases related to cell death such as disease of degenerative cranial nerve system, apoplexy, cancer, immune disorders or inflammation, and CIA gene is effective for a gene theraphy of the same diseases.

6 Claims, 14 Drawing Sheets

FIG. 1

SEQUENCE LISTING

<160> NUMBER OF SEQ ID NOS: 11

<210> SEQ ID NO 1
<211> LENGTH: 27
<212> TYPE: DNA
<213> ORGANISM: Artificial Sequence
<220> FEATURE:
<223> OTHER INFORMATION: CIA-ASP

<400> SEQUENCE: 1
gggagcggga gaagtatgac aacatgg     27

<210> SEQ ID NO 2
<211> LENGTH: 25
<212> TYPE: DNA
<213> ORGANISM: Artificial Sequence
<220> FEATURE:
<223> OTHER INFORMATION: CIA-Bam

<400> SEQUENCE: 2
ggatgttcca cgggatcccg gctac     25

<210> SEQ ID NO 3
<211> LENGTH: 920
<212> TYPE: DNA
<213> ORGANISM: Mouse CIA gene

<400> SEQUENCE: 3
ctcgagctgc cgatcgggtt tcccggcagg cgcaggcgga aaaagcgagc accgagcttc     60
tgtcgccatc tccgggactc caaacgcccc aggtctcttg tgctgtatag ctgcctgggc    120
ctgcaggatg ttccacggga tcccggctac tcctggtgtt ggagcccctg ggaacaagcc    180
ggagctgtat gaggaagtaa agctctacaa gaatgctcgg gagcgggaga agtatgacaa    240
catggcagag ctctttgccg tggtgaagac gatgcaggcc ctggagaagg cgtacatcaa    300

-continued

```
ggactgtgtc accccccaatg agtacactgc agcctgctcc aggctcctgg tccagtacaa    360
agctgccttc cgacaggtcc aaggctcaga gatcagctcc attgatgaat tttgccgaaa    420
gttcagactg gactgcccac ttgctatgga gaggatcaaa gaggaccggc ccatcactat    480
caaagacgac aagggcaatc tcaaccgctg cattgcagat gttgtttcgc tcttcattac    540
agtcatggac aagctgcgtc tggagatccg tgccatggac gagattcagc cagacctgcg    600
ggagctgatg gagacaatgc acagaatgag ccacctgcct ccagacttcg agggccgcca    660
gacagtcagc cagtggctgc agaccctgag tggtatgtcg gcctctgacg agctggatga    720
ctctcaagtt cgccagatgc tcttcgatct ggagtccgct acaacgcct ttaaccgctt    780 cctacacgcc taagcctcac cgagacagga atgagagtgg tagagatgtg acgactcagc    840
cccccagtgt gtctacatcc gtcctagatg cctatattgt caggatatca cccacaataa    900
atatttgtct aaccttcaaa                                                920
```

<210> SEQ ID NO 4
<211> LENGTH: 221
<212> TYPE: PRT
<213> ORGANISM: Mouse CIA Protein

<400> SEQUENCE: 4

```
Met Phe His Gly Ile Pro Ala Thr Pro Gly Val Gly Ala Pro Gly Asn
  1               5                  10                  15

Lys Pro Glu Leu Tyr Glu Val Lys Leu Tyr Lys Asn Ala Arg Glu
             20                  25                  30

Arg Glu Lys Tyr Asp Asn Met Ala Glu Leu Phe Ala Val Val Lys Thr
         35                  40                  45

Met Gln Ala Leu Glu Lys Ala Tyr Ile Lys Asp Cys Val Ser Pro Asn
     50                  55                  60

Glu Tyr Thr Ala Ala Cys Ser Arg Leu Val Gln Tyr Lys Ala Ala
 65                  70                  75                  80

Phe Arg Gln Val Gln Gly Ser Glu Ile Ser Ile Asp Glu Phe Cys
                 85                  90                  95

Arg Lys Phe Arg Leu Asp Cys Pro Leu Ala Met Glu Arg Ile Lys Glu
            100                 105                 110

Asp Arg Pro Ile Thr Ile Lys Asp Lys Gly Asn Leu Asn Arg Cys
        115                 120                 125

Ile Ala Asp Val Val Ser Leu Phe Ile Thr Val Met Asp Lys Leu Arg
130                 135                 140

Leu Glu Ile Arg Ala Met Asp Glu Ile Gln Pro Asp Leu Arg Glu Leu
145                 150                 155                 160

Met Glu Thr Met His Arg Met Ser His Leu Pro Pro Asp Phe Glu Gly
                165                 170                 175

Arg Gln Thr Val Ser Gln Trp Leu Gln Thr Leu Ser Gly Met Ser Ala
            180                 185                 190

Ser Asp Glu Leu Asp Asp Ser Gln Val Arg Gln Met Leu Phe Asp Leu
        195                 200                 205

Glu Ser Ala Tyr Asn Ala Phe Asn Arg Phe Leu His Ala
    210                 215                 220
```

<210> SEQ ID NO 5
<211> LENGTH: 26
<212> TYPE: DNA
<213> ORGANISM: Artificial Sequence
<220> FEATURE:

<223> OTHER INFORMATION: CIA-H1

<400> SEQUENCE: 5
cccagagcct agaggatgtt tcatgg 26

<210> SEQ ID NO 6
<211> LENGTH: 24
<212> TYPE: DNA
<213> ORGANISM: Artificial Sequence
<220> FEATURE:
<223> OTHER INFORMATION: CIA-H2

<400> SEQUENCE: 6
ccgggctcag gcatgcagga agcg 24

<210> SEQ ID NO 7
<211> LENGTH: 913
<212> TYPE: DNA
<213> ORGANISM: Human CIA Gene

<400> SEQUENCE: 7

```
attcggcagg aggcgcgcgt gccaggtctc agtgctgtgc cccccagag  cctagaggat     60
gtttcatggg atcccagcca cgccgggcat aggagcccct gggaacaagc cggagctgta    120
tgaggaagtg aagttgtaca agaacgcccg ggagagggag aagtacgaca acatggcaga    180
gctgtttgcg gtggtgaaga caatgcaagc cctggagaag gcctacatca aggactgtgt    240
ctcccccagc gagtacactg cagcctgctc ccggctcctg gtccaataca agctgccttt    300
caggaggtcg cagggctcag aaatcagctc tattgacgaa ttctgccgca agttccgcct    360
ggactgcccg ctggccatgg agcggatcaa ggaggaccgg cccatcacca tcaaggacga    420
caagggcaac ctcaaccgct gcatcgcaga cgtggtctcg ctcttcatca cggtcatgga    480
caagctgcgc ctggagatcc gcgccatgga tgagatccag cccgacctgc gagagctgat    540
ggagaccatg caccgcatga gccacctccc acccgacttt gagggccgcc agacggtcag    600
ccagtggctg cagaccctga gcggcatgtc ggcgtcagat gagctggacg actcacaggt    660
gcgtcagatg ctgttcgacc tggagtcagc ctacaacgcc ttcaaccgct tcctgcatgc    720
ctgagcccgg gcactagccc ttgcacagaa gggcagagtc tgaggcgatg gctcctggtc    780
ccctgtccgc cacacaggcc gtggtcatcc acacaactca ctgtctgcag ctgcctgtct    840
ggtgtctgtc tttggtgtca gaactttggg ccgggcccct ccccacaata aagatgctct    900
ccgaccttca aaa                                                       913
```

<210> SEQ ID NO 8
<211> LENGTH: 221
<212> TYPE: PRT
<213> ORGANISM: Human CIA Protein

<400> SEQUENCE: 8

```
Met Phe His Gly Ile Pro Ala Thr Pro Gly Ile Gly Ala Pro Gly Asn
 1               5                  10                  15

Lys Pro Glu Leu Tyr Glu Val Lys Leu Tyr Lys Asn Ala Arg Glu
             20                  25                  30

Arg Glu Lys Tyr Asp Asn Met Ala Glu Leu Phe Ala Val Val Lys Thr
         35                  40                  45

Met Gln Ala Leu Glu Lys Ala Tyr Ile Lys Asp Cys Val Ser Pro Ser
     50                  55                  60

Glu Tyr Thr Ala Ala Cys Ser Arg Leu Leu Val Gln Tyr Lys Ala Ala
```

-continued

```
                65                  70                  75                  80

Phe Arg Arg Ser Gln Gly Ser Glu Ile Ser Ser Ile Asp Glu Phe Cys
                        85                  90                  95

Arg Lys Phe Arg Leu Asp Cys Pro Leu Ala Met Glu Arg Ile Lys Glu
                       100                 105                 110

Asp Arg Pro Ile Thr Ile Lys Asp Lys Gly Asn Leu Asn Arg Cys
                       115                 120                 125

Ile Ala Asp Val Val Ser Leu Phe Ile Thr Val Met Asp Lys Leu Arg
                130                 135                 140

Leu Glu Ile Arg Ala Met Asp Glu Ile Gln Pro Asp Leu Arg Glu Leu
       145                 150                 155                 160

Met Glu Thr Met His Arg Met Ser His Leu Pro Pro Asp Phe Glu Gly
                       165                 170                 175

Arg Gln Thr Val Ser Gln Trp Leu Gln Thr Leu Ser Gly Met Ser Ala
                       180                 185                 190

Ser Asp Glu Leu Asp Asp Ser Gln Val Arg Gln Met Leu Phe Asp Leu
                       195                 200                 205

Glu Ser Ala Tyr Asn Ala Phe Asn Arg Phe Leu His Ala
       210                 215                 220
```

<210> SEQ ID NO 9
<211> LENGTH: 209
<212> TYPE: PRT
<213> ORGANISM: Arabidopsis thaliana

<400> SEQUENCE: 9

```
       Met Glu Val Lys Leu Trp Asn Asp Lys Arg Glu Arg Glu Met Tyr Glu
        1               5                  10                  15

Asn Phe Ala Glu Leu Tyr Ala Ile Ile Lys Ala Thr Glu Lys Leu Glu
                        20                  25                  30

Lys Ala Tyr Ile Arg Asp Leu Ile Ser Pro Ser Glu Tyr Glu Thr Glu
                    35                  40                  45

Cys Gln Lys Leu Ile Val His Phe Lys Thr Leu Ser Ala Ser Leu Lys
                50                  55                  60

Asp Met Val Pro Asn Ile Glu Arg Phe Ala Glu Thr Tyr Lys Met Asp
       65                  70                  75                  80

Cys Ser Ala Ala Val Tyr Arg Leu Val Thr Ser Gly Val Pro Ala Thr
                        85                  90                  95

Val Glu His Arg Ala Ala Ala Ser Ala Ser Thr Ser Ser Ser Ala Ser
                       100                 105                 110

Val Val Ala Glu Cys Val Gln Asn Phe Ile Thr Ser Met Asp Ser Leu
                       115                 120                 125

Lys Leu Asn Met Val Ala Val Asp Gln Val Tyr Pro Leu Leu Ser Asp
                130                 135                 140

Leu Ser Ala Ser Leu Asn Lys Leu Ser Ile Leu Pro Pro Asp Phe Glu
       145                 150                 155                 160

Gly Lys Ile Lys Met Lys Glu Trp Leu Leu Arg Leu Ser Lys Met Gly
                       165                 170                 175

Ala Ser Asp Glu Leu Thr Glu Gln Gln Ala Arg Gln Leu His Phe Asp
                       180                 185                 190

Leu Glu Ser Ser Tyr Asn Ser Phe Met Ala Ala Leu Pro Asn Ala Gly
                       195                 200                 205

Asn
```

<210> SEQ ID NO 10
<211> LENGTH: 242
<212> TYPE: PRT
<213> ORGANISM: Saccharomyces cerevisiae

<400> SEQUENCE: 10

```
Met Gln Lys His Asn Ile Lys Leu Asn Gln Asn Gln Asp Ile Ser Gln
 1               5                  10                  15

Leu Phe His Asp Glu Val Pro Leu Phe Asp Asn Ser Ile Thr Ser Lys
            20                  25                  30

Asp Lys Glu Val Ile Glu Thr Leu Ser Glu Ile Tyr Ser Ile Val Ile
        35                  40                  45

Thr Leu Asp His Val Glu Lys Ala Tyr Leu Lys Asp Ser Ile Asp Asp
    50                  55                  60

Thr Gln Tyr Thr Asn Thr Val Asp Lys Leu Leu Lys Gln Phe Lys Val
65                  70                  75                  80

Tyr Leu Asn Ser Gln Asn Lys Glu Glu Ile Asn Lys His Phe Gln Ser
                85                  90                  95

Ile Glu Ala Phe Cys Asp Thr Tyr Asn Ile Thr Ala Ser Asn Ala Ile
            100                 105                 110

Thr Arg Leu Glu Arg Gly Ile Pro Ile Thr Ala Glu His Ala Ile Ser
        115                 120                 125

Thr Thr Thr Ser Ala Pro Ser Gly Asp Asn Lys Gln Ser Ser Ser Ser
    130                 135                 140

Asp Lys Lys Phe Asn Ala Lys Tyr Val Ala Glu Ala Thr Gly Asn Phe
145                 150                 155                 160

Ile Thr Val Met Asp Ala Leu Lys Leu Asn Tyr Asn Ala Lys Asp Gln
                165                 170                 175

Leu His Pro Leu Leu Ala Glu Leu Leu Ile Ser Ile Asn Arg Val Thr
            180                 185                 190

Arg Asp Asp Phe Glu Asn Arg Ser Lys Leu Ile Asp Trp Ile Val Arg
        195                 200                 205

Ile Asn Lys Leu Ser Ile Gly Asp Thr Leu Thr Glu Thr Gln Ile Arg
    210                 215                 220

Glu Leu Leu Phe Asp Leu Glu Leu Ala Tyr Lys Ser Phe Tyr Ala Leu
225                 230                 235                 240

Leu Asp
```

<210> SEQ ID NO 11
<211> LENGTH: 248
<212> TYPE: PRT
<213> ORGANISM: Schizosaccharomyces pombe

<400> SEQUENCE: 11

```
Met Thr Glu Tyr Tyr Asp Leu Asn Leu Leu Glu Lys Glu Thr Ser Glu
 1               5                  10                  15

Glu Asn Asn Phe His Thr Lys Asn Gln Gln Val Arg Glu Asp Leu Ser
            20                  25                  30

Ile Leu Tyr Ser Ile Leu Val Ala Leu Glu Gln Leu Glu Lys Ala Phe
        35                  40                  45

Thr Lys Asp Ala Val Ser Thr Ser Asp Phe Asn Ser Thr Cys Glu Leu
    50                  55                  60

Leu Ile Gln Gln Trp Glu Ser Cys Phe Ser Asp Glu Arg Val Thr Gln
65                  70                  75                  80

Ala Phe Gly Ser Phe Glu Asp Phe Cys Ser Lys Tyr Arg Leu Gln Cys
                85                  90                  95
```

-continued

```
Pro Arg Ala Ile Lys Arg Ile Gln Glu Gly Ile Ser Asp Glu Arg Ser
            100                 105                 110

Gln Ser Asn Ser Thr Phe Ser Asn Ala Ile Ser Thr Thr Ala Glu Pro
        115                 120                 125

Ser Ile Ala Met Asn Asp Thr Thr Pro Gln Thr Val Asn Pro Thr Lys
        130                 135                 140

Ala Pro Ser Asn Pro Ser Ala Ser Ile Ala Lys Ser Ile Ala Gly Leu
145                 150                 155                 160

Val Gln Asn Phe Ile Thr Thr Leu Asp Ala Ile Arg Leu Asn Phe Ile
            165                 170                 175

Ala Lys Asp Gln Leu His Pro Leu Leu Ser Glu Leu Ile Val Ser Met
            180                 185                 190

Asp Asp Leu Thr Glu Ser Leu Lys Ile Gln Val Ser Cys Arg Asn Lys
        195                 200                 205

Leu Val Gln Trp Leu Ile Lys Ile Asn Asn Met Asn Ile Thr Asp Gln
        210                 215                 220

Leu Asn Asp Val Glu Lys Arg Glu Leu Leu Tyr Asp Leu Glu Gln Ala
225                 230                 235                 240

Tyr Ala Glu Cys Tyr Ser Leu Leu
            245
```

MOUSE CIA PROTEIN AND CIA GENE HAVING ANTI-APOPTOTIC ACTIVITY AS A SELECTIVE INHIBITOR OF CAD INTERACTING ASK1 USE THEREOF

FIELD OF THE INVENTION

The present invention relates to a novel protein that shows an anti-apoptotic function. More particularly, the present invention relates to a novel protein, which is inhibitory of both CAD and ASK1 activities, thus negatively regulating CAD- and ASK1-mediated apoptosis pathway. Also, the present invention relates to a gene encoding the protein and uses of the protein in gene therapy.

BACKGROUND

Apoptosis or programmed cell death (PCD) is a genetically regulated mechanism of active cell death observed during development and disease and is required for homeostasis in multicellular organisms. There is a distinct and precisely localized control over the fate of specific cells that undergo apoptosis in a mixed cell population. Apoptosis is a selective process for self-elimination of damaged or undesired cells in various biological systems. This event, similar to proliferation, is tightly regulated with both processes playing essential roles in the homeostasis of renewable tissues. If apoptosis is under inappropriate control, various diseases such as cancer, autoimmune diseases and neurodegenerative diseases are caused (Kerr et al, Br. J. Cancer, 16, 239–257, 1972). Apoptosis is characterized by morphological and biochemical changes, causing the damage of cell junctions in cells, nuclear membrane blebbing, and cell shrinkage in the early stage, and chromatin condensation, cytoplasmic and nuclear condensation, mitochondrial membrane potential loss, the change of cytoplasmic membrane compositions, and the formation of apoptotic bodies in the late stage. As a final event of the cells undergoing apoptosis, internucleosomal DNA degradation into nucleosomal fragments is the most dramatic and fatal biochemical feature (Green D. R., and Reed, J. C., Science, 281, 1309–1312, 1998).

Extensive research has revealed key players and mechanisms involved in apoptosis in various organisms. For example, nematodes such as *Canorhabdtis elegans* are reported to have three molecules playing important roles in controlling apoptosis: CED-3, CED-4 and CED-9. Both of CED-3 and CED-4 are indispensable for the induction of apoptosis, while CED-9, which shares amino acid sequence homology with mammalian Bcl2 family proteins, acts as an inhibitor of CED-4, which is the nematode homologue of the mammalian Apaf-1. Particularly, CED-3 is known to have the same function as that of caspase family proteins of cystein, aspartate specific proteases.

Execution of apoptosis is mediated by members of the caspase family. After an apoptotic stimulus is received, the zymogen form of the caspase is rapidly activated by proteolytic processing at highly related aspartic acid cleavage sites to generate the heteromeric subunits of the active protease. Once activated by various apoptotic stimuli, the caspase family of proteins decomposes cellular proteins such as RAPD (poly(ADP-ribose) polymerase), lamine, cytokeratins, and inhibitor of caspase-activated deoxyribonuclease (ICAD) to mediate apoptosis (Cryns, V., and Yuan, J., Genes Dev., 12, 1551–1570, 1998). Conditions associated with the apoptosis mediation of caspases include receptor-mediated signal transduction, depletion of growth factors, oxidative stress, DNA damage, and disruption of cell—cell adhesion or cell-matrix interaction. As a result of the active research directed to the caspase family, at least 14 different caspases have been found in mammalian cells. Basically, caspases are cysteine proteases that cleave after aspartic acid residues, which are required for the initiation and execution of apoptosis. That is, caspases have an absolute requirement in the target substrate sequence with cleavage occurring at the carbonyl end of the aspartic acid residue (Nunez et al., Oncogene, 17, 3272–3245, 1998).

DNA fragmentation, a hallmark of apoptosis, is an irreversible event closely associated with caspase activation. In the cells undergoing apoptosis, nuclear DNA is degraded into DNA fragments of 180–200 bp in size by endogenous endonucleases, which show a ladder-like pattern when run on an agarose gel. Functioning as the endogenous endonuclease, CAD (caspase-activated DNase), also called CPAN (caspase activated DNase) and DFF (DNA fragmentation factor), has been recently isolated from human and murine cells (Liu et al., Proc. Natl. Acad. Sci. U.S.A., 95, 1841–1846, 1998; Liu et al., Cell, 89, 175–184, 1997). DFF is a heterodimeric protein complex consisting of DFF45 (molecular weight 45 kDa) and DFF40 (molecular weight 40 kDa). Purified DFF40 alone possesses intrinsic nuclease activity, which is inhibited by its association with DFF45. The proteolytic cleavage of DFF45 by caspase-3 frees DFF40 to function as a nuclease. Mouse homologue of human DFF was identified as a DNase inhibitor designated ICAD, for inhibitor of caspase-activated DNase. As in DFF, CAD remains inactive while being associated with ICAD. Upon cleavage of ICAD, a caspase activated deoxyribonuclease (CAD) is released, activated and eventually causes the degradation of DNA in the nuclei. Therefore, ICAD, which consists of 331 amino acids, is the mouse counterpart of the human DFF45. ICAD has been recently found to exist in a long form (ICAD-L) and a short form (ICAD-S). Two different ICAD cDNAs (ICAD-L and ICAD-S) were isolated from a mouse T-cell lymphoma cDNA library. These cDNAs contained open reading frames of 331 and 265 amino acids, respectively. The two cDNAs were identical up to amino-acid position 261, after which the sequences differ (ICAD-S has four characteristic C-terminal amino acid residues), suggesting that the ICAD-L and ICAD-S messenger RNAs are generated through alternative splicing (Sakahira et al., J. Biol. Chem., 274, 15740–15744, 1998).

CAD/DFF40 is produced as a complex with ICAD/DFF45: treatment with caspase-3 releases the DNase activity that causes DNA fragmentation in nuclei. ICAD/DFF45 therefore seems to serve as a molecular chaperone for inducing an appropriate folding of CAD/DFF40 during its synthesis, as well as functioning as a selective inhibitor of CAD/DFF40. CAD/DFF40 is inactive while being complexed with ICAD/DFF45. The inhibition of the nuclease activity of CAD/DFF40 by ICAD/DFF45 can be broken by caspase-3: cleavage of ICAD/DFF45 at both Asp positions 117 and 224 by caspase-3 inactivate ICAD/DFF45, allowing CAD/DFF40 to be active as an endonuclease (Mcllroy et al., Oncogene, 18, 4401–4408, 1999). Of the caspases identified so far, caspase-3 and caspase-7 are known to inactivate ICAD/DFF45 by cleavage in vitro. However, caspase-7 is reported to be unable to produce the active form of CAD/DFF40: caspase-3 is regarded as an important mediator for CAD-dependent DNA fragmentation (Wolf et al., J. Biol. Chem., 274, 30651–30656, 1999). Another group involved in the activation of CAD/DFF40 is exemplified by CIDEs whose N-terminal region CIDE-N is found to be conserved in ICAD/DFF45 (Inhohara et al., EMBO. J., 17, 2526–2533, 1998).

There exist MAPK (mitogen-activated protein kinase) signaling pathways that are closely related to apoptotic cell death (Cobb, M. H., and Go.dsmith, E. J., J. Biol. Chem., 270, 14843–14846, 1995; Dickens et al., Science, 277, 693–696, 1997). Triggered by extracellular sitimuli, MAPK signaling pathways are known to control a number of genes taking part in cell cycle control. Typically, a well-defined three-kinase module composed of a MAPK, a MKPK kinase (MAPKK) and a MAPKK kinase (MAPKKK), which act in a cascade pattern, is involved in each MAPK signaling pathway. In the MAPK cascade, MAPKKK is activated by an upstream kinase or an adaptor protein and then phosphorylates MAPKK which then becomes its active form, leading to MAPK activation. Activated MAPK moves into the nucleus and phosphorylates downstream kinases, thereby it regulates gene expression or other cellular events.

At least three MAPK cascades have been identified in mammals, each consisting of the three-kinase module. These cascades play key roles in relaying various physiological, environmental or pathological signals from the extracellular environment to the transcriptional machinery in the nucleus, for which extracellular signal-regulated kinase (ERK), c-jun N-terminal kinase/stress-activated protein kinase, and p38 MAPK are responsible, respectively (Boulton et al., Cell, 65, 663–675, 1991; Cobb, M. H., and Goldsmith, E. J., J. Biol. Chem., 270, 14843–14846, 1995; Fringer et al., Curr. Opin. Genet. Dev., 7, 67–74, 1997; Han et al., Science, 265, 808–811, 1994).

Before playing a role in growth factor-mediated activation and differentiation, ERK is activated in cells upon stimulation with mitogenic factors, such as insulin, epidermal growth factor (EGF), and phorbol ester. One of the MAPKs, JNK stimulates the transcriptional activity of c-Jun preferentially in response to proinflammatory cytokines, and certain environmental stresses, such as UV light, heat shock, or osmotic stress (Ahmed, A., and Salahuddin, A., Indian. J. Biochem. Biophys., 31, 156–159, 1994; Derijard et al., Science, 267, 682–685, 1994; Galcheva-Gargova et al., Science, 265, 806–808, 1994). Activation of p38 kinase, which is highly homologous to yeast HOG1 kinase, is induced by high osmotic pressures, lipopolysaccharide, TNF-α, and interleukin-1 (Han et al., Science, 265, 808–811, 1994; Rouse et al., Cell, 78, 1027–1037, 1994).

Of the signaling pathways, JNK and p38 cascades are suggested to play important roles in the apoptotic cell death caused by various stresses (Butterfield et al., J. Biol. Chem., 272, 10110–10116, 1997; Kawadaki et al., J. Biol. Chem., 272, 18518–18521, 1997). Three jnk genes, jnk1, jnk2 and jnk3, have been isolated thus far (Gupta et al., EMBO. J., 15,2760–2770, 1996; Widmann et al., Physiol. Rev. 79, 143–180, 1999) and are found to be activated by two MAPKKs, MKK4/SEK1 (Derijard et al., Cell, 76, 1025–37, 1999) and MKK7 (Holland et al., J. Biol. Chem., 272, 24944–24948, 1997). As for p38 kinase, its four genes, p38a, p38b, p38c and p38d, were cloned (Gpedert et al., EMBO. J., 16, 3563–357, 1997; Han et al., Science, 265, 808–811, 1994; Jiang et al., J. Biol. Chem., 272, 30122–30128, 1997; Lee et al., Nature, 272, 23668–23674, 1994; Wang et al., J. Biol. Chem., 272, 23668–23674, 1997) and all are activated by MKK3 and MKK6. Various MAPKKKs have been identified as upstream activators in the JNK and p38 cascades. Of them, TAK1 (tumor growth factor-activated kinase 1) activates both of the JNK and p38 cascades (Gerwins et al., J. Biol. Chem., 272, 8288–8285, 1997; Takekawa et al., EMBO. J., 16, 4973–4982, 1997; Yamaguchi et al., Science, 270, 2008—2008–2011, 1995).

Also, a novel MAPKKK was recently identified and designated as ASK1 (for apoptosis signal-regulating kinase 1). ASK1 is reported to activate two different subgroups of MAPKK, SEK1/MKK4 and MKK3/MAPKK6/MKK6, which in turn activate stress-activated protein kinase (JNK) and p38 MAP kinase, respectively (Ichijo et al., Science, 275, 90–94, 1997; Yamaguchi et al., Science, 270, 2008–2011, 1996). That is, ASK1 activates the SEK1-JNK pathway and the MKK3/6-p38 pathway, selectively. In addition to the apoptosis caused by stresses such as $H_2O_2$, UV light and other DNA-damaging agents, ASK1 plays an important role in TNFα- and Fas-induced apoptosis, according to previous reports (Hsu et al., Immunity, 4, 387–396, 1996; Rothe et al., Cell, 83, 1243–1252, 1994; Shu et al., Proc. Natl. Acad. Sci. U.S.A., 93, 13973–13978, 1996). ASK1 is activated by TNFR and Fas through the interaction between the C-terminal non-catalytic region of ASK1 and the conserved C-terminal TRAF domain of the TRAF family TRAF2 (Hoeflich et al., Oncogene, 18, 5814–5820, 1999) and through the interaction with Fas-associated protein Daxx (Chang et al., Science, 281, 1860–1863, 1998). The Daxx-induced ASK1 activation stimulates both the JNK and p38 pathways, leading to apoptotic cell death (Chang et al., Science, 281, 1860–1863, 1998; Yang et al., Cell, 89, 1067–1076, 1997). ASK1, therefore, acts as a common mediator of TNFα- and Fas-induced signal cascades and study on proteins and molecular mechanisms controlling the activity of ASK1 will help understand apoptosis processes better.

Leading to the present invention, the intensive and thorough research on the ASK1-mediated apoptosis pathway, conducted by the present inventors, resulted in the finding that CAD is inhibited by a mouse protein that can interact with ASK1. The protein, named CAD inhibitor interacting with ASK1 (abbreviated to "CIA"), is found to directly interact with ASK1 to inhibit ASK1-mediated apoptosis. In addition, CIA is identified to bind to CAD to inhibit CAD-mediated DNA fragmentation. Therefore, the novel CIA gene or its protein functions as a selective inhibitor of CAD- and ASK1-mediated apoptosis. Based on its intracellular functions, the CIA gene or protein can be used as a therapeutic agent for treatment of degenerative diseases of the cranial nervous system, apoplexy, cancer, immune disorders and inflammation.

SUMMARY OF THE INVENTION

It is an object of the present invention to provide novel materials capable of regulating stress-induced apoptosis.

It is another object of the present invention to provide uses of the novel materials in treating apoptosis-related diseases.

In one aspect of the present invention, there is provided a mouse CIA protein and a cDNA coding for the protein.

In another aspect of the present invention, there is provided a method for searching for DNA sequences or proteins interacting with a CIA gene and a CIA protein or their analogs, in which the CIA gene or protein is used as a probe.

In a further aspect of the present invention, there is provided a therapeutic agent for use in the gene therapy of apoptosis-related diseases, comprising a gene construct containing the mouse CIA gene as a therapeutically active ingredient.

In still a further aspect of the present invention, there is provided a pharmaceutical composition for the treatment of apoptosis-related diseases, comprising the mouse CIA protein as a therapeutically effective ingredient.

BRIEF DESCRIPTION OF THE DRAWINGS

FIG. 1 is a diagram showing amino acid sequences of the mouse CIA (CAD inhibitor interacting with ASK1) protein and its homologs derived from human and yeast.

DETAILED DESCRIPTION OF PREFERED EMBODIMENTS

Figure 2:
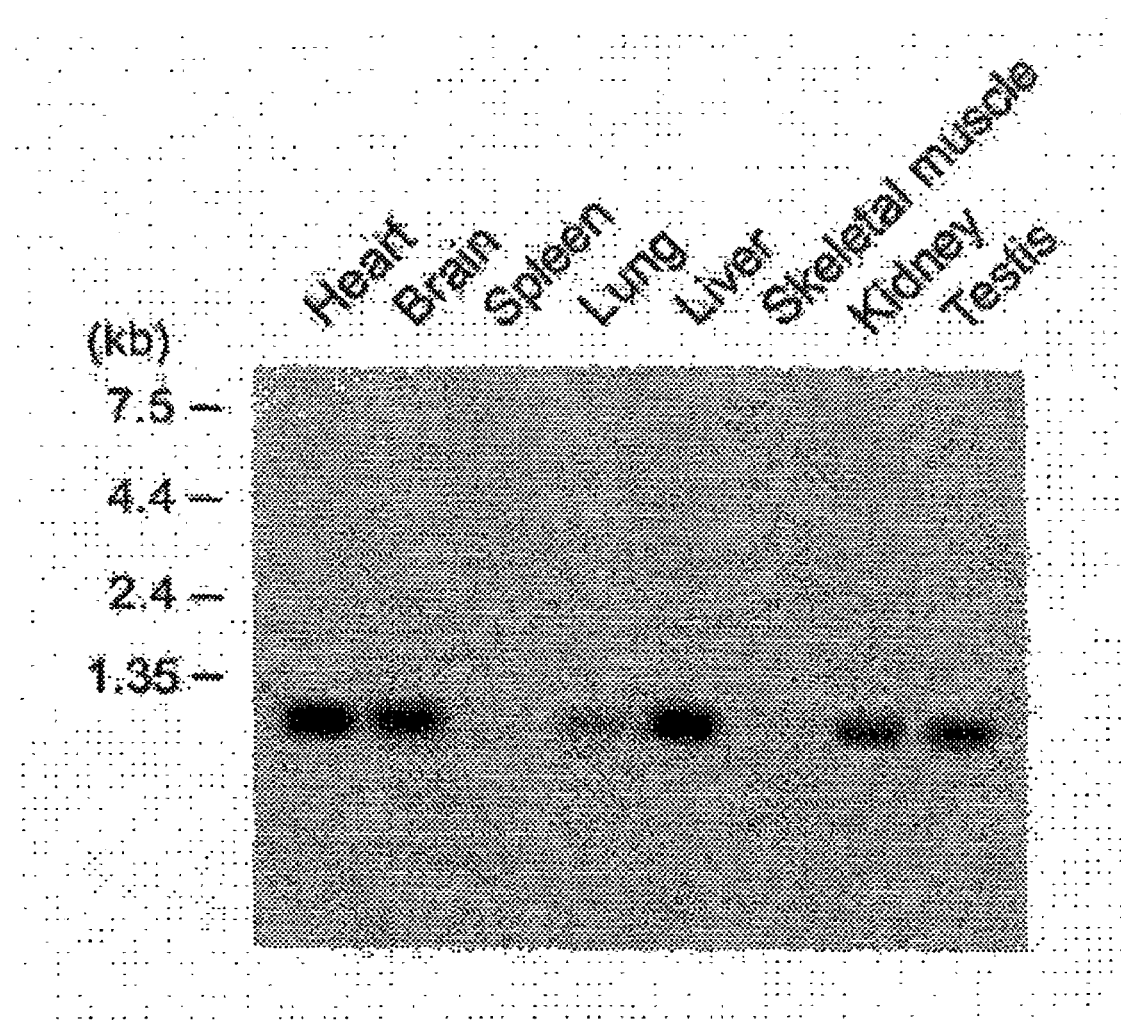
FIG. 2 is a photograph showing the distribution of mouse CIA transcripts by using multiple tissue Northern blot analysis.

The present invention provides a mouse CIA gene having the base sequence of SEQ. ID. No.3, its homologs and variants. And also, the present invention provides a mouse CIA protein having the amino acid sequence of SEQ. ID. No. 4 or its variants.

The term "homologs" of the CIA gene as used herein means all genes containing base sequences coding for the mouse CIA protein of SEQ. ID. No. 4. Hence, all kinds of genetic materials capable of producing the mouse CIA protein of SEQ. ID. No. 4 fall within the scope of the present invention.

The term "variants" of the mouse CIA protein as used herein means all mutant proteins resulting from the deletion, addition, insertion or substitution of at least one amino acid in the mouse CIA protein of SEQ. ID. No. 4, but limited to proteins having 80% or higher homology in total with the mouse CIA protein and 90% or higher homology partially with the mouse protein at an N-terminal region from amino acid 1 to 79 and at a C-terminal region from amino acid 174 to 221.

The term "variants" of the mouse CIA gene as used herein means any base sequence coding for the variants of the mouse CIA protein.

In the present invention, a yeast two-hybrid system using ASK1 is adopted to find a protein that associates with ASK1 and its gene. Also, its function is identified in vivo and in vitro. The novel protein, designated CIA, is found to act as a negative regulator of apoptosis by inhibiting CAD and ASK1, as will be described later. On the whole, since the production of transgenic animals and the studies on mutants through gene targeting are usually conducted in mice, the mouse CIA gene of the present invention is useful for the same purposes.

To isolate a mouse protein that can bind specifically to ASK1, $2 \times 10^6$ yeast clones prepared from a mouse brain cDNA library were screened using the full-length ASK1 as bait. A clone having a 0.9 kb DNA insert that showed association with the bait was found and sequenced.

With the aim of securing a mouse cDNA clone that has a complete 5' region, 5'-RACE (5'-rapid amplification of cDNA ends) PCR was conducted to produce a 930 bp DNA fragment which was identified to have a complete ORF (open reading frame). Base sequencing analysis revealed that the CIA cDNA clone consists of 920 nucleotides of SEQ. ID. No. 3 with an ORF of 666 nucleotides coding for 221 amino acids of SEQ. ID. No. 4. Also, no in-frame stop codons were found within the 5'-untranslated region (UTR) of the mouse CIA.

Figure 1:
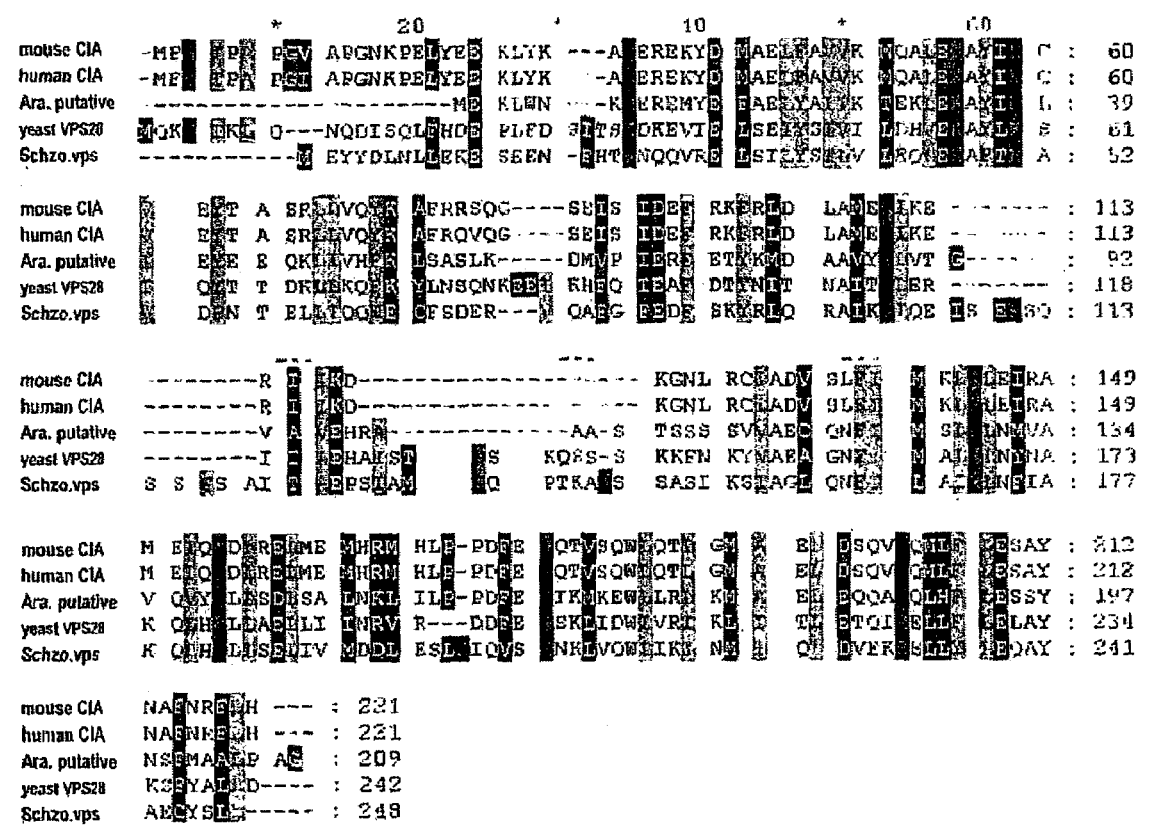

Based on the amino acid sequence of the mouse CIA protein, a human CIA clone was isolated by RT-PCR. The human CIA gene produced by RT-PCR was identified as the base sequence of SEQ. ID. No. 7 whose amino acid sequence has 99% or higher homology with the mouse CIA protein (see FIG. 1). As a result of a BLAST homology search in GeneBank, the mouse CIA of SEQ. ID. No. 4 showed 35% homology to a putative protein from *Arabidopsis thaliana* and 28% homology to *Saccharomyces cerevisiae* VPS28 and *Schizosaccharomyces pombe* putative VPS and has no known protein domain motifs (see FIG. 1).

In accordance with a further embodiment of the present invention, there is provided a method for searching for DNA sequences or proteins interacting with CIA gene or CIA protein, or their gene or protein analogs, in which the mouse CIA gene or any of its homologs or variants, or the mouse CIA protein or any of its variants is used as a probe.

The term "analogs" of the mouse CIA protein or CIA gene as used herein means proteins or DNA sequences whose randomly selected 30 bases or 10 amino acids show 80% or higher homology to corresponding parts of the CIA gene of SEQ. ID. No. 3 or the CIA protein of SEQ. ID. No. 4. The term "interacting" with CIA protein as used herein means capable of physical association with CIA protein directly or indirectly.

The term "probe" as used herein means any of the probes available for Sourthern blot analysis, Northern blot analysis, Western blot analysis, far Western blot, gel mobility shift analysis, library screening, and affinity chromatography, as well as including the probe available to DNA chips for automatic analysis and primers used for PCR. In other words, probes usable in all assays based on nucleic acid-nucleic acid, protein—protein, or protein-nucleic acid ineractions are included. For use in the present invention, the probes may be labeled with radioactive isotopes or fluorescent materials.

Preferably, the method for searching for nucleic acid materials or proteins is performed according to the analysis processes suggested above. For example, PCR is performed using a partial base sequence of the CIA gene of the present invention as a primer, and the PCR product is used as a probe to screen analogs of the CIA gene against cDNA libraries. Another example is to perform affinity chromatography, in which the CIA protein immobilized onto resins is used to search for proteins capable of binding physically thereto.

In accordance with still a further embodiment of the present invention, there is provided a pharmaceutical composition for use in gene therapy, comprising a gene construct containing the mouse CIA gene as a pharmaceutically active ingredient.

Provided as a means for effectively expressing the gene of interest, that is, a CIA gene or its homolog or variant, the gene construct might be modified in structure according to concrete purposes of gene therapy. For example, when gene therapy is performed by increasing or decreasing the expression of the endogenous CIA gene, the gene construct may contain transposons for homogenous recombination near the CIA gene anchored thereat. On the other hand, gene therapy mediated through the effective expression of exogenous mouse CIA gene can be achieved by use of a gene construct in which a potent promoter is provided to a CIA gene or its homolog or analog. Basically, the structure of the gene construct is dependent on gene therapy method. For example, if gene therapy follows viral infection, the gene construct is based on vectors derived from viral genomes of, e.g., retroviruses.

The therapeutic agent for gene therapy of the present invention can be used for the treatment of diseases resulting from the loss of control of cell death processes, such as cancers, degenerative diseases of the cranial nervous system, apoplexy, diseases of the immune system, and inflammation, as well as the treatment of diseases resulting from the loss of control of apoptosis processes owing to congenital or acquired genetic defects. Observation of decreased CAD and ASK1 activity in the mammalian cells that have high expression levels of CIA ensures the application of the promising therapeutic agent of the present invention to the diseases.

In accordance with still another embodiment of the present invention, there are provided an inhibitor of CAD- and ASK1-mediated apoptosis, comprising the mouse CIA protein or its variant as an active ingredient, and a therapeutic agent for treatment of apoptosis-related diseases, comprising the mouse CIA protein or its variant as an active ingredient.

With the mouse CIA protein or its variant, the inhibitor can be used to selectively inhibit CAD- and ASK1-mediated apoptosis, as well as the signal transduction pathways in which CAD or ASK1 takes part.

Exemplified by cancers, degenerative cranial nervous system diseases, apoplexy, immune system diseases, inflammation and apoptosis-related diseases are associated with abnormal control of apoptosis.

The inhibitor or therapeutic agent may be administered orally or parenterally. Preferable is a parenteral injection. The inhibitor or therapeutic agent may be used with various dosage forms for oral or parenteral administration. For formulation, pharmaceutically acceptable diluents, expedients and/or carriers may be used, including fillers, thickeners, binders, wetting agents, disintegrants, surfactants, etc.

When the inhibitor or therapeutic agent are to be formulated into solid forms, they are exemplified by tablets, pills, troches, powders, granules, capsules, or other dosage forms for oral administration. To prepare these solid dosage forms, the CIA protein or its variant may be added with at least one of expedients, such as starch, calcium carbonate, sucrose, lactose and/or gelatin. Apart from simple expedients or carriers, lubricants such as magnesium stearate, may be added for the formulation of the protein. Useful as liquid forms to the oral administration of the CIA protein are suspensions, emulsions, syrups and other usually used dosage forms for internal use. In this regard, not only simple diluents, such as water and liquid paraffin, but also various expedients, such as wetting agents, sweeteners, aromatic agents, preservatives, etc., may be used. Dosage forms for parenteral administration include sterile aqueous solutions, non-aqueous solvents, suspensions, emulsions, freeze-dried agents, suppositories, etc. For formulation of non-aqueous solvents and suspensions, vegetable oils such as propylene glycol and polyethylene glycol, or injectable esters such as ethyl oleate, may be used. As bases for suppositories, witepsol, macrogol, Tween 61, cocoa butter, laurinic acid, and glycerogelatine are useful.

Depending on the conditions of the patient, the effective dose of the mouse CIA protein or its variants ranges from 1 to 10 mg per kg of body weight and preferably from 1 to 5 mg per kg of body weight.

In the present inventions the mouse CIA gene and protein are biologically and biochemically characterized, thereby determining uses thereof. First, the CIA protein of the present invention is found to associate directly with an N-terminal region of ASK1 to block the apoptosis pathway downstream of ASK1. In addition, the CIA protein binds directly to CAD to block DNA fragmentation. That is, the novel protein CIA, identified and characterized by the present invention, is a potent anti-apoptotic factor, which inhibits ASK1 activity in the early stage of apoptosis and CAD in the later stage of apoptosis.

After CIA clones were selected from a mouse brain cDNA library by a yeast two-hybrid system using ASK1 as a bait, multiple tissue Northern blot analysis was conducted with the aim of determining the tissue specific and complex hybridization patterns of the CIA gene, identifying the presence of CIA transcripts in heart, brain, liver and testis (see FIG. 2).

Western blot analysis is useful to determine the expression level of CIA. In the present invention, CIA is found to be expressed in the mouse brain and various cell lines, including L929, NIH3T3, H4, HeLa and COS-7 (see FIG. 3).

For use in determining the domains or motifs of CIA and ASK1, which are essential for the interaction therebetween, various deletion mutants of a GST-CIA fusion protein and a radio-labeled ASK1 protein were produced. In vitro binding assay results show that C-terminal region of CIA binds physically to N-terminal region of ASK1 to inhibit stress- or cytokine-induced ASK activation (see FIG. 4).

To prove the ability of CIA to inhibit the activity of ASK1, ASK1-Flag was expressed, along with GST-MKK6, in the absence or presence of His-CIA. ASK1 activity was inhibited in a dose-dependent pattern by CIA as measured by a immunecomplex kinase assay (see FIG. 5).

Also, CIA was identified as an ASK1 inhibitor in the stress-induced and in the TRAF2-mediated activation of ASK1. In this regard, ASK1 activity was quantitatively assayed using GST-MKK6 as a substrate by immunecomplex of ASK1 from 293 cells, which were exposed to UV light or allowed to overexpress TRAF2 after being transfected with an expression vector containing ASK1 (see FIG. 6). The ectopic expression of CIA resulted in the inhibition of the enzyme activity of ASK1, thus negatively affecting the kinase activity of JNK1, which is located downstream of ASK1 (see FIGS. 7 and 8). The inhibitory effect of CIA on ASK1-mediated JNK/SAPK activation was also confirmed by the transcription efficiency of c-Jun measured in terms of luciferase activity, which was significantly increased by ASK1, but decreased as CIA was co-expressed (see FIG. 8).

Besides, a yeast two-hybrid system using CAD responsible for apoptotic DNA fragmentation as a bait was adopted to isolate a protein capable for physical association with CAD. Positive clones obtained by screening human and murine brain cDNA libraries were found to have the base sequences identical to those of the CIA proteins isolated as ASK1-interacting proteins. Accordingly, CIA can interact physically with CAD that plays an important role in apoptotic DNA fragmentation, as well as serving as an inhibitor of ASK1. Consequently, CIA inhibits apoptosis by selectively interacting with ASK1 and CAD.

For use in determining the domains or motifs of CIA and CAD, which are essential for the interaction therebetween, various deletion mutants of a GST-CIA fusion protein and a radio-labeled CAD protein were constructed. In vitro assay results show that an N-terminal region of CIA binds physically to the N-terminal CIDE domain of CAD/DFF40, which is conserved in CIDEs (see FIG. 9).

Figure 10:
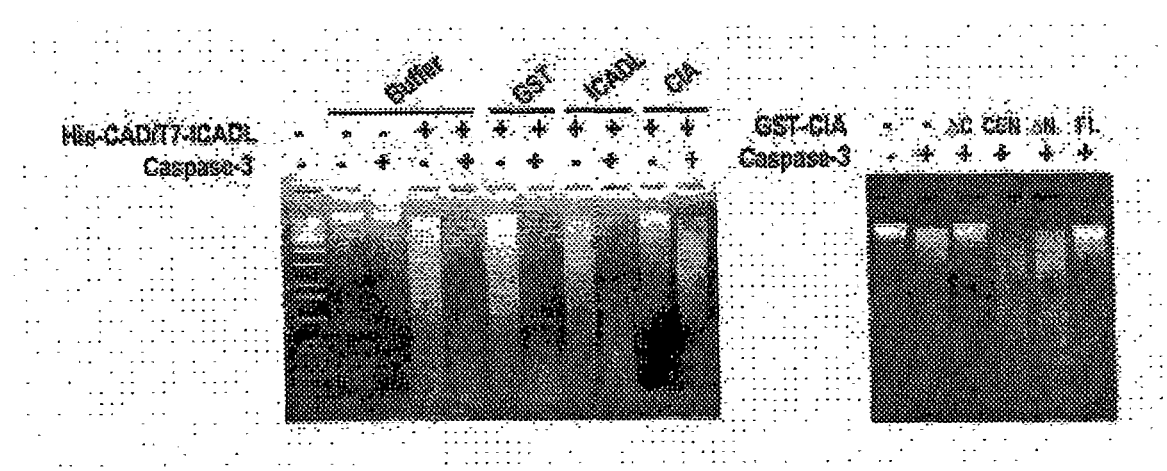
FIG. 10 is photographs showing the results of electrophoresis identifying the inhibitory activity of CIA against nuclease activity of CAD in vitro.

Reaction of His-CAD/T7-ICAD recombinant protein with the GST-fusion CIA or its deletion mutant recombinant proteins was performed in the presence or absence of recombinant caspase-3 in nuclease reaction buffer to confirm the inhibitory activity of CIA against in vitro CAD nuclease activity (see FIG. 10). For examining the inhibitory effect of CIA on DNA fragmentation in vivo, an HA-tagged CIA clone or its deletion mutants were co-transfected, together with CAD-Flag or ICADL, into 293 cell lines in the presence or absence of caspase-3 (see FIG. 11). In these two experiments, it is concluded that CIA is a CAD inhibitor whose inhibitory activity against the nuclease activity and DNA fragmentation by CAD is performed by the direct protein—protein interaction.

Stable expression of CIA in mammals (see FIG. 12) can disclose much concerning its functions in vivo. In 293 cell lines, CIA acts as a negative regulator against stress-induced or JNK/SAPK-mediated apoptosis by inhibiting both ASK1 and CAD activities (see FIGS. 13 and 14).

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Screening of Mouse CIA Protein Binding Specifically to ASK1

<1-1> Yeast 2-Hybrid Screening

Using the full-length form of ASK1, the yeast 2-hybrid screening method was performed to isolate a mouse protein that can bind specifically to ASK1. First, the full-length ASK1 cDNA was fused into the LexA DNA binding domain of pLexA bait plasmid (Clonetech), which was then inserted into *Saccharomyces cerevisiae* EGY48 [p8op-lacZ] (Clonetech). The yeast transformant thus obtained was used to screen 2×106 clones against the mouse brain cDNA library (Stratagene) cloned into the pB42AD pray plasmid (Clonetech) For use as probes, the cDNA clones isolated by the yeast 2-hybrid screening were labeled with a $^{32}$P radioactive isotope by a random priming method with the aid of Prime-It II random primer labeling kit (Stratagene). A filter on which the mouse brain Lamda ZAP II cDNA library phage plaques were replicated was immersed for 2 hours in a prehybridization buffer (5×SSPE, 5× Denhardt's solution, 0.15% SDS, 50% formamide and 100 μg/ml denatured salmon sperm DNA) and then incubated, together with the probe, for 12 hours or longer at 42° C. After being washed, the filter was stored at −70° C. in contact with an X-ray film backed by an intensifying screen. Based on the spots developed on the X-ray film, positive phage clones were isolated. Positive cDNA inserts were cloned into the EcoRI site of pBluescript SK(−) (Stratagene) phagemid, followed by base sequencing to identify a 0.9 kb CIA cDNA. Using this cDNA clone as a probe, the total RNA isolated from the adult mouse brain was subjected to Nothern blot analysis. As a result, a hybrid mRNA band of about 10 kb was detected.

<1-2> 5′-RACE

While the cDNA clone served as template, 5′-RACE (5′-rapid amplification of cDNA ends) (Boeringer Mannheim) was performed against the total mRNA isolated from mouse brain tissues to yield a CIA cDNA of the 5′ region. In this regard, there was used a set of primers consisting of CIA-GSP of SEQ. ID. No. 1 and CIA-Bam of SEQ. ID. No. 2. The PCR product thus obtained was cloned into pBluescript SK(−).

Base sequencing analysis revealed that the CIA cDNA clone is 930 bp long and contains a complete open reading frame (ORF). The clone with a 666 bp ORF was identified to consist of 930 bases of SEQ. ID. No. 3 and have no in-frame stop codons in the 5′-untranslated region. In addition, the ORF of the cDNA base sequence was analyzed to encode a mouse CIA protein consisting of 221 amino acids of SEQ. ID. No. 4.

<1-3> Isolation of Human CIA Clone

In order to isolate a human counterpart of the mouse CIA-clone, the CIA-H1 primer of SEQ. ID. No. 5 and the CIA-H2 primer of SEQ. ID. No. 6 were prepared on the basis of the EST clone having high homology with the cDNA base sequence. RT-PCR, in which the total RNA prepared from human fetal brain tissues was used as a substrate in the presence of the primer set, produced a DNA sequence. It was identified through base sequencing that the human DNA sequence consists of 913 nucleotides of SEQ. ID. No. 7. Based on SEQ. ID. No. 7, the amino acid sequence of the human CIA protein was found to show 99% or higher homology to that of the mouse CIA protein, as shown in FIG. 1.

<1-4> Amino Acid Sequence of Mouse CIA

A BLAST homology search in GeneBank databases indicated that the mouse CIA of SEQ. ID. No. 4 has 35% homology with a putative protein from *Arabidopsis thaliana* and 28% homology with *Saccharomyces cerevisiae* VPS28 and *Schizosaccharomyces pombe* putative VPS, and has no known protein domain motifs, as shown in FIG. 1.

Example 2

Expression and Distribution Pattern of Mouse CIA Gene in Tissues

<2-1> Multiple Tissue Northern Blot Analysis

To examine the expression pattern of the mouse CIA gene isolated in Example 1, multiple tissue Northern blot analysis was performed by use of a Northern blot kit (Clonetech). In detail, the mouse CIA cDNA was labeled with 32P radioactive isotope by a random priming method using Prime-It II random primer labeling kit and used as a probe to hybridize with mouse multiple tissue blots containing poly (A)+ RNA (2 μg each) isolated from various mouse tissues. The Northern blot analysis results are given in FIG. 2.

As seen in FIG. 2, a CIA mRNA transcript with a length of 1 kb was expressed at high levels in various tissues including heart, brain, liver and kidneys, but at very low levels in spleen, lungs and skeletal muscles.

<2-2> Western Blot Analysis

An examination was made of the expression level of the CIA protein through Western blot analysis using an anti-CIA antiserum.

The first thing to do was to subclone the mouse CIA cDNA prepared in Example 1 into pTrcHisC (Invitrogen). Thereafter, the expression vector was transformed into *E. coli* DH5α to express a His6-tagged CIA protein. From the *E. coli* transformant, a His6-tagged CIA protein was isolated, and then purified before immunization to rabbits so as to obtain an anti-CIA anti-serum containing polyclonal antibodies. Cell lysate aliquots, each containing 30 μg of proteins, prepared from mouse brain and various mammalian cell lines, were electrophoresed and blotted with the anti-serum.

Figure 3:
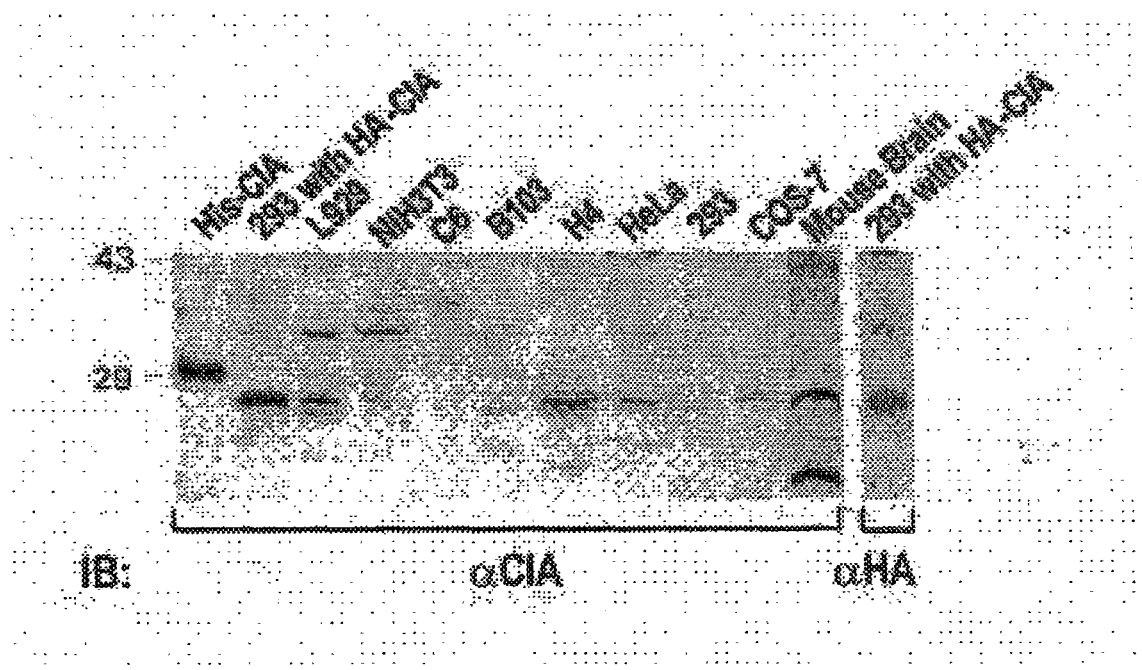
FIG. 3 is a photograph showing the result of Western blot analysis using anti-CIA antisera wherein the CIA is expressed in various mammalian cell lines and mouse brain tissue.

The resulting Western blots are shown in FIG. 3. As seen in FIG. 3, a CIA protein with a molecular weight of about 25 kDa was detected in the mouse brain and various mammalian cell lines including L929, NIH3T3, H4, HeLa and COS-7.

Example 3

Assay for In Vitro Binding of CIA to ASK1

To examine which site of the CIA protein interacts with ASK1, various deletion CIA mutants tagged by GST were prepared.

In detail, DNA fragments which encode deletion mutant forms of CIA, that is, CIA-ΔN deficient in N-terminal amino acids 1 to 78, CIA-ΔC deficient in C-terminal amino acids 175 to 221, and CIA-CEN containing only amino acids 79 to 174, deficient in both N- and C-terminal regions, were prepared from the full-length form of the CIA wild type peptide (CIA-WT) by PCR (polymerase chain reaction) and then cloned into pGEX-4T-1 (Pharmacia). In this regard, GST residues were tagged to the N-terminus of each of the DNA fragments and the CIA wild-type peptide. The resulting recombinant expression vectors were introduced into *E. coli* BL21 (DE3), which was then cultured. Following the induction of the expression of the recombinant proteins corresponding to the DNA fragments in the presence of 1 mM IPTG, centrifugation was performed to obtain cell pellets, which were then suspended in cell lysis buffer (50 nM Tris-HCl, pH 8.0, 100 mM EDTA, 1% Triton X-100, 1 mM PMSF, and 0.5 mM DTT) and subjected to ultrasonication. After five repetitions of the cell lysis process, cell lysates were centrifuged to obtain supernatants, from which the GST-tagged recombinant proteins were separated and purified by use of glutathione-agarose.

Separately, ASK1 wild-type and its mutant forms, ASK1-ΔN deficient in N-terminal amino acids 1 to 649, ASK1-ΔC deficient in C-terminal amino acids 936 to 1375, and ASK1-NT from amino acid 1 to 656, were prepared as above and labeled with $^{35}$S-methionine, followed by in vitro transcription and translation with the aid of a reticulocyte lysate TNT system (Promega).

After being immobilized onto glutathione-agarose beads, GST-CIA-WT and its deletion recombinant peptides were reacted with the in vitro-transcribed [$^{35}$S] methionine-labeled ASK1 or its mutant peptides at 4° C. for 3 hours in a buffer (50 mM Tris, pH 7.5, 150 mM NaCl, 2 mM EDTA, 1 mM dithiothreitol, 0.1% NP-40 and 5 mg/ml BSA). After completion of the reaction, the glutathione-agarose beads were washed three times with a buffer (50 mM HEPES, pH 7.5, 150 mM NaCl, 1 mM EDTA, 1 mM dithiothreitol, 0.1% Tween 20). Next, $^{35}$S-labeled peptides were eluted from the glutathione-agarose beads and analyzed by SDS-PAGE.

Figure 4:
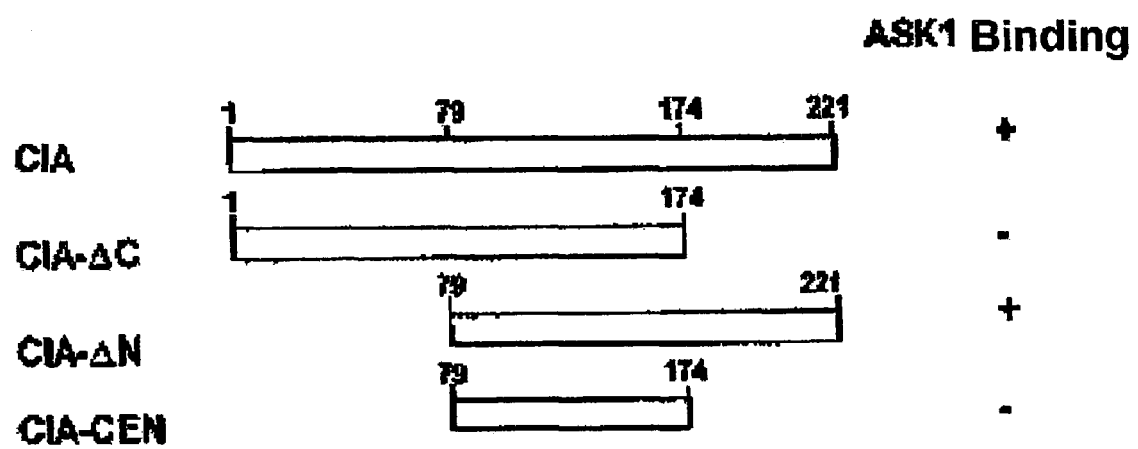
FIG. 4 is diagrams showing full-length CIA, ASK1 and their deletion mutant constructs, along with their binding ability in vitro, identifying a C-terminal region of CIA and an N-terminal region of ASK1 as binding motifs.
Figure 4:
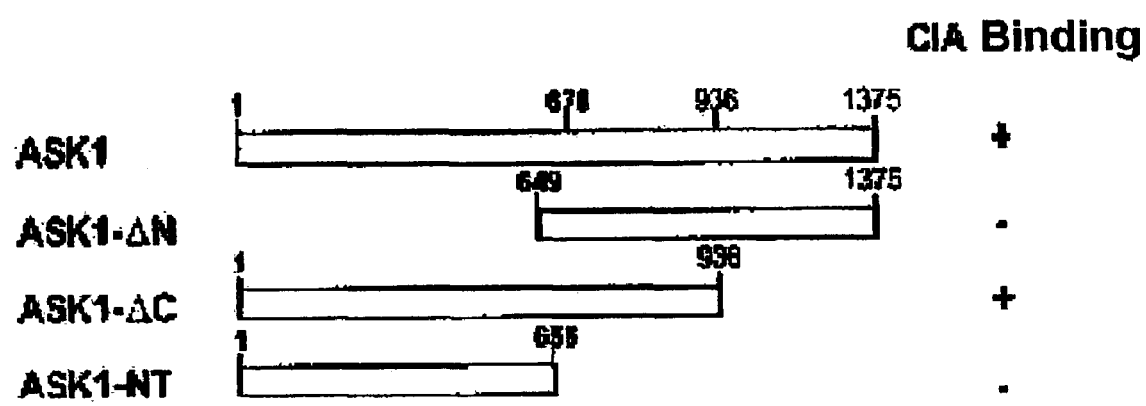

The analysis results are given in FIG. 4, along with wild-type peptides and various truncated peptides used. As seen in FIG. 4, the wild type CIA (CIA-WT) and the N-terminal region-deleted CIA peptide (CIA-ΔN) were found to bind physically to the in vitro-translated $^{35}$S-labeled ASK1, whereas the C-terminal region-deleted CIA peptide (CIA-ΔC), the CIA mutant peptide containing only the N-terminus (CIA-NT) and the CIA mutant peptides deficient in both terminal regions (CIA-CEN) did not interact with ASK1. As for the binding motif of CIA, it was present in the full length ASK1 and the ASK1 mutants containing the N-terminal region (ASK1-NT) or deficient in the C-terminal region (ASK1-ΔC) as demonstrated by the interaction of CIA with them. However, the ASK1 mutant deficient in the N-terminus (ASK1-ΔN) did not bind to CIA.

Consequently, the C-terminal region of CIA and the N-terminal region of ASK1 are necessary for the interaction therebetween.

Example 4

Inhibitory Effect of CIA on ASK1 Kinase Activity

<4-1> Novel ASK1 Inhibitor CIA

Generally, ASK1, which acts as a MAPK kinase kinase (MAPKKK) in the JNK/SAPK and p38 signal tranduction pathways, were known to be activated upon cell's exposure to stress. Based on this fact and the direct interaction between CIA and ASK1 identified in Example 3, an examination was made of the ability of CIA to inhibit the kinase activity of ASK1.

In this regard, a cDNA clone of ASK1 (granted from Dr. Ichijo, Tokyo Univ. Japan) was inserted into the EcoRI/XbaI restriction site of pcDNA3-Flag (Invitrogen) to make a recombinant expression vector pcDNA3-ASK1-Flag, which was then introduced into the mammalian 293 cell line. Irradiation of the transformed cells with 80 J/m$^2$ of UV light induced the kinase activity of ASK1. Then, the transformed cells were lysed in buffer A (20 mM Tris-HCl, pH 7.4, 150 mM sodium chloride, 1% Triton X-100, 1% deoxycholate, 12 mM β-glycerphosphate, 10 mM sodium florids, 5 mM EGTA and 1 mM PMSF), followed by the centrifugation of the lysate at 12,000×g at 4° C. for 15 min. Immunoprecipitation was induced by adding anti-Flag mouse monoclonal antibody (Boehringer Mannheim Inc.) to the supernatant.

This reaction solution was further added with Protein-G sepharose™ beads (Pharmacia), after which careful mixing was carried out at 4° C. for 1 hour. The immunocomplexes thus formed were washed three times with buffer A. As for ASK1, its activity was assayed by use of the GST-MKK6 (K82A) isolated in the presence of His-CIA. The results are given in FIG. 5.

Figure 5:
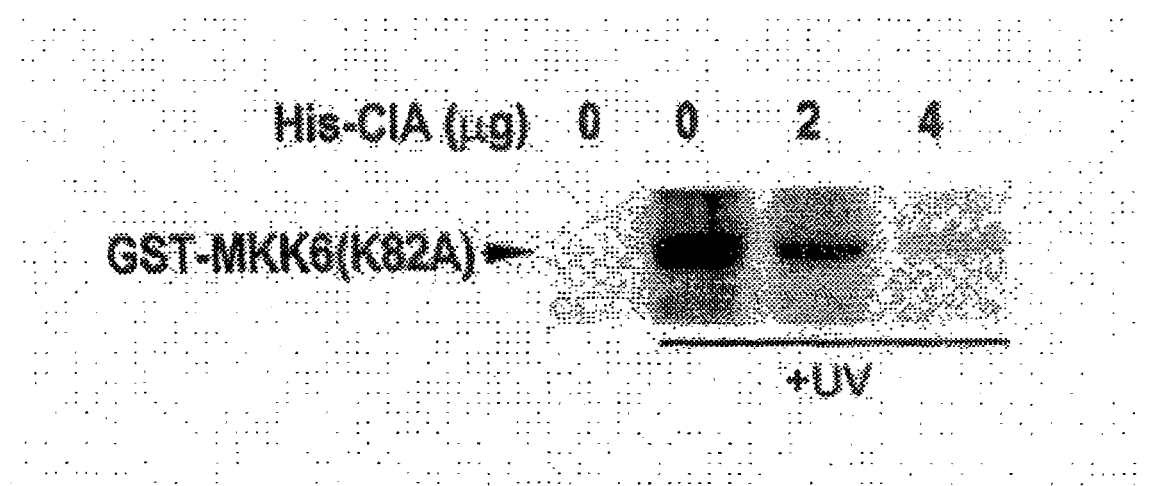
FIG. 5 is a photograph showing the result of immunoprecipitation using anti-Flag antibody, identifying the interaction of CIA with ASK1 in 293 cells.

When the HIS-CIA recombinant protein was absent, as shown in FIG. 5, the phosphorylation of GST-MKK6 was strongly induced by the kinase activity of the ASK1 activated by UV irradiation. The presence of the HIS-CIA recombinant protein, however, lowered the kinase activity of ASK1, which had been activated by the UV irradiation, resulting in a significant decrease in the phosphorylation of GST-MKK6.

Therefore, the CIA protein acts as an inhibitor of ASK1 while still being not phosphorylated by ASK1.

<4-2> Effect of Ectopic CIA on Intracellular Activity of ASK1

An examination was made of the inhibitory activity of CIA against ASK1 kinase activity in mammalian cells. Three expression vectors anchoring ASK1-Flag, CIA and TRAF-2 (granted from David Goeddel, Tularik Inc. USA), respectively, were co-transfected into the 293 cell line. 48 hours after the transfection, the cells were exposed to UV light at 80 J/m2 or not. Following the lysis of the cells, immunoprecipitation was conducted using the mouse anti-Flag monoclonal antibody in the same manner as that of Example 4-1. The ASK1 activity of the resulting immunocomplexes were determined by their kinase activity. The results are given in FIG. 6.

Figure 6:
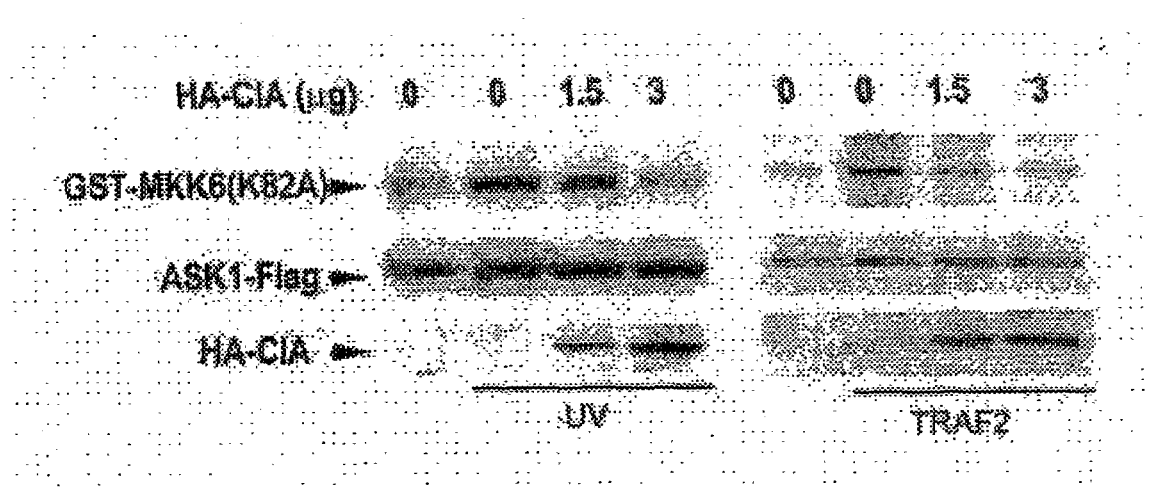
FIG. 6 is a photograph showing that the ectopic expression of CIA inhibits the kinase activity of ASK1 in 293 cells.

As seen in FIG. 6, the co-expression of CIA inhibited the kinase activity of ASK1 induced by UV exposure or by the expression of TRAF-2, an activator of ASK1, thereby blocking the phosphorylation of GST-MKK 6 in a dose-dependent manner, like the results of Example 4-2.

These results, taken together, show that CIA acts as an inhibitor of ASK1, both in vitro and in vivo.

<4-3> Inhibitory Effect of CIA on ASK1-Mediated JNK/SAPK Activation

One of the main downstream effects of ASK1 is the activation of JNK/SAPK to promote the transcriptional activity of c-jun. An examination was made of the effect of CIA, functioning as an inhibitor of ASK1, on the activation of JNK/SAPK.

Initially investigated was the effect of CIA on the kinase activity of JNK1. In this regard, expression vectors anchoring ASK1, HA-SAPKβ (Shim et al., Nature, 381, 804–806, 1996) and CIA, respectively therein were co-transfected into 293 cell line. 48 hours after the transfection, the cells were lysed, and the lysate was subjected to immunoprecipitation using an anti-HA antibody in the same manner as in Example 4-1. To determine the SAPKβ activity of the immunocomplexes, their kinase activity was examined. Next, the effect of CIA on the transcriptional activity of c-Jun was examined. To this end, 293 cell line was transiently transfected with expression vectors pFR-Luc (Clonetech), pFA2-c-jun (Clonetech), pcDNA3-CIA, pcDNA3-ASK1 and pcDNA3-β-gal (Invitrogen). 48 hours after the transfection, cells were lysed, and aqueous fractions obtained from the lysate were assayed for luciferase activity by use of a luciferase assay kit (Promega). The luciferase assay was based on the β-galactosidase activity of the same cell.

Figure 7:
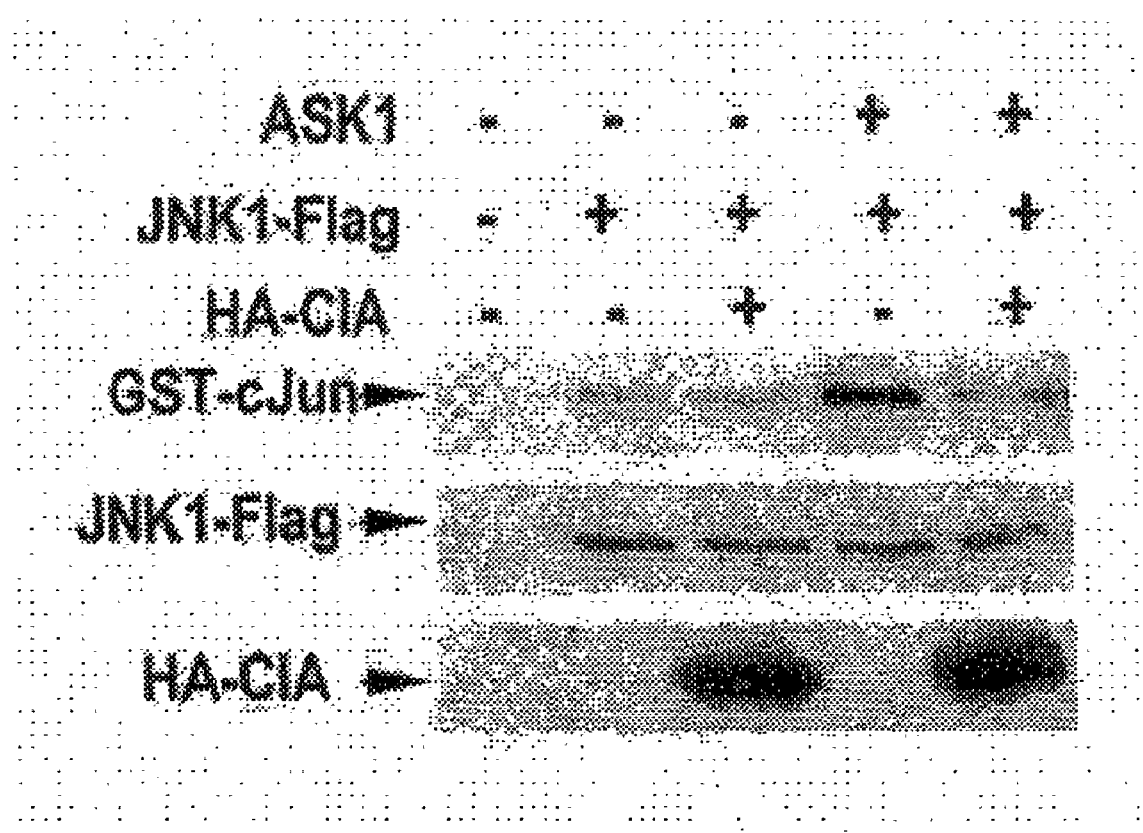
FIG. 7 is a photograph showing the result of immunocomplex kinase analysis, demonstrating the inhibitory activity of CIA against the enzyme activity of JNK induced by ASK1.
Figure 8:
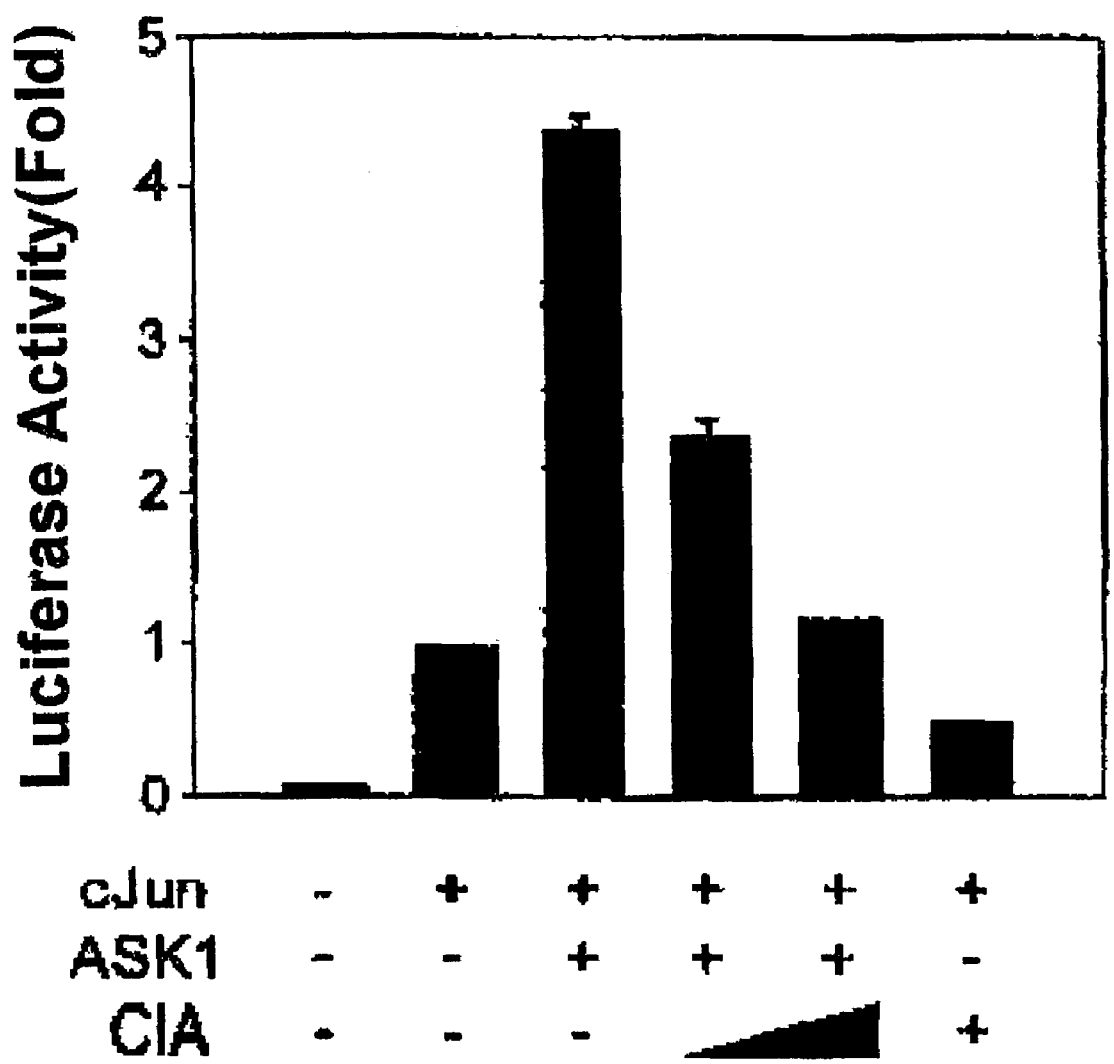
FIG. 8 is a graph showing the inhibitory activity of CIA against ASK1-mediated c-Jun activity in terms of luciferase activity.

The ectopic expression of CIA inhibited the enzyme activity of ASK1, and thus negatively affected the kinase activity of JNK1, which is located downstream of ASK1, as shown in FIG. 7. In addition, the transcription efficiency of c-Jun measured in terms of luciferase activity was significantly increased by ASK1, but decreased as CIA was co-expressed, as shown in FIG. 8. Consequently, CIA directly inhibits the activity of ASK1, thereby regulating the kinase activity of downstream signal controlling proteins.

Example 5

CIA as a CAD-Interacting Protein

CAD (caspase-activated deoxyribonuclease), which is the mouse counterpart of the human DFF40, is known to play an important role in apoptotic DNA fragmentation. With this fact in mind, an attempt was made to isolate proteins, which can interact with CAD. Using a mouse CAD gene as a probe, yeast 2-hybrid screening was conducted on human fetal brain and adult mouse brain cDNA libraries in the same manner as in Example 1-1. As a result, 8 positive clones were selected from the transformants of human fetal brain cDNA library and 9 positive clones from the transformants of adult mouse brain cDNA library. It was determined through Base sequencing and GeneBank analysis that the clones have the same base sequence as that of CIA isolated as an ASK1-interacting protein. These results indicate that the CIA of the present invention, functioning as an inhibitor of ASK1, can interact physically with CAD at least partially involved in DNA fragmentation, and therefore can act as a controller of apoptosis.

Example 6

Assay for Binding of CIA to CAD

To examine which site of the CIA protein interacts with CAD, various CIA deletion mutants tagged by GST were prepared.

In detail, wild type CIA (CIA-WT) and its deletion mutants, CIA-ΔN, CIA-ΔC and CIA-CEN, all of them prepared in Example 4, were immobilized onto glutathione-agarose beads and then applied to in vitro translated [$^{35}$S] methionine-labeled CAD. Meanwhile, wild type CAD (CAD-WT) (1–345) and its deletion mutants, CAD-ΔN deficient in a C-terminal region (Δ1–83), CAD-NT containing N-terminal half only (Δ162–345), CAD-ΔC deficient in a C-terminal region (Δ290–345), were prepared by PCR and cloned to pLexA (Clonetech). After being isolated and purified from E. coli transformants harboring the expression vectors, the recombinant proteins CAD-WT, CAD-ΔN, CAD-NT and CAD-ΔC, were labeled with $^{35}$S radioactive isotope, and then applied to the glutathione-agarose beads onto which GST-CIA was immobilized. The proteins bounded to the glutathione-agarose beads were eluted, and separated on a gel by SDS-PAGE.

Figure 9:
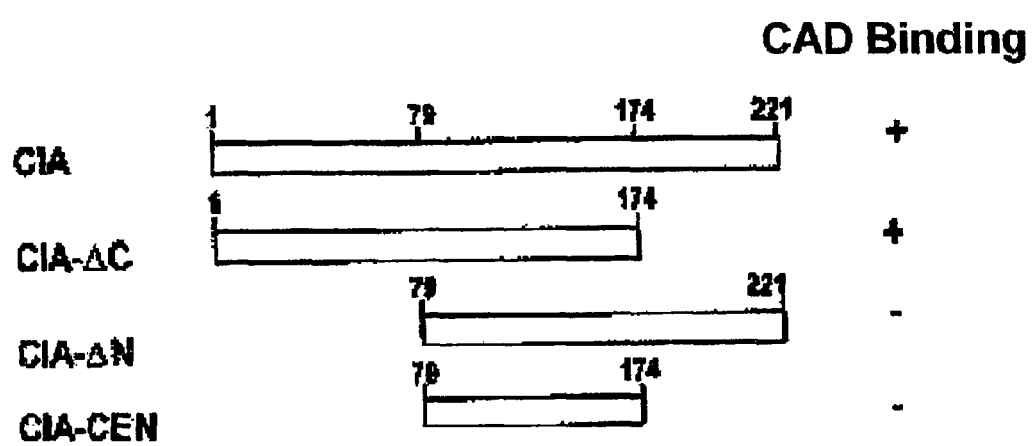
FIG. 9 is diagrams showing full-length CIA, CAD and their deletion mutant constructs, along with their binding ability in vitro, identifying the interaction of the N-terminal region of CAD with the CIDE-N domain of CAD.
Figure 9:
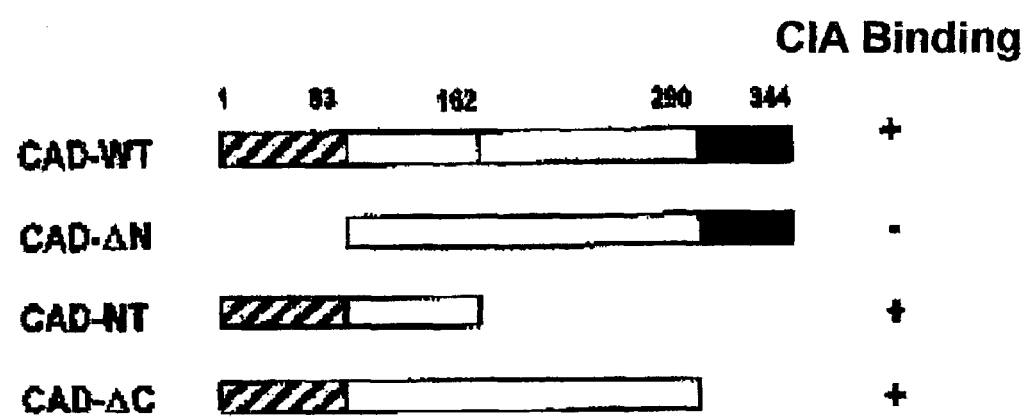

The analysis results are given in FIG. 9, along with wild type peptides and various truncated peptides used. As seen in FIG. 9, the wild type CIA (CIA-WT), the C-terminal region-deleted CIA peptide (CIA-ΔC) and the CIA mutant peptide containing only the N-terminus (CIA-NT) were found to bind physically to the in vitro-transcribed $^{35}$S-labeled CAD, whereas the N-terminal region-deleted CIA peptide (CIA-ΔN), and the CIA mutant peptide deficient in both terminal regions (CIA-CEN) did not interact with $^{32}$P-labeled CAD. These results indicate that the recombinant CIA proteins can be directly associated with CAD and the N-terminal domain of CIA is responsible for this association.

Generally, it is known that CAD N-terminal amino acids 1 to 83, which have homology to the conserved CIDE-N domain, mediate the interaction of CAD with ICAD, while the C-terminal amino acids 290 to 345 are required for the nuclease activity of CAD. The interaction between CIA and CAD was confirmed in the binding assay using wild type CAD and its deletion mutant recombinant proteins. As shown in FIG. 9, GST-fusion CAD-WT, CAD-NT containing an N-terminal half only and CAD-ΔC deficient in a C-terminal region bound to [$^{35}$S] methionine-labeled CIA clones, but CAD-ΔN did not.

Taken together, the results described above demonstrate that CIA inhibits the activity of CAD by the specific interaction between N-terminal domains of CIA and CAD.

Example 7

Inhibitory Effect of CIA on CAD Activity and DNA Fragmentation

<7-1> Inhibition of CIA Against In Vitro CAD Nuclease Activity

A His-CAD/T7-ICAD recombinant protein was made to examine the inhibitory effect of CIA on in vitro CAD nuclease activity. To this end, ICAD tagged by T7 at its C-terminus was cloned into the EcoRI/NotI restriction site of pET23b (Novagene) and CAD tagged by His at the C-terminus was inserted into the XbaI restriction site of the same vector. The resulting recombinant plasmid construct pET23b-His-CAD/T7-ICAD was transformed into E. coli BL21 (DE-3) (Pharmacia), which was then cultured for 3 hours in the presence of 1 mM IPTG to induce the expression of two proteins. The recombinant proteins expressed in E. coli transformant were isolated by use of Ni-NTA column (Quiagen) and purified to homogeneity for use in the following experiments.

The isolated and purified His-CAD/T7-ICAD recombinant protein (1 μg) was reacted with the GST-fusion CIA or its deletion mutant recombinant proteins (2 μg) at 37° C. for 2 hours in the presence or absence of recombinant caspase-3 (200 ng) in nuclease reaction buffer (10 mM HEPES, pH 7.5, 1 mM EGTA, 5 mM MgCl$_2$, 50 mM NaCl, 1 mg/ml bovine serum albumin). After completion of the reaction, the samples were run on 2% agarose gel in an electric field and dyed with ethidium bromide.

The electrophoresis results are given in FIG. 10. As seen in FIG. 10, GST-CIA inhibited the nuclease activity of the CAD recombinant protein. Particularly even in the presence of caspase-3, which reacts with ICAD to induce the nuclease activity of CAD, GST-CIA was found to inhibit the nuclease activity of CAD. On the contrary, GST-ICADL did not show any inhibitory activity in the presence of caspase-3. According to the in vitro nuclease assay using CIA wild-type and its deletion mutant recombinant proteins, GST-CIA-WT and GST-CIA-ΔC strongly inhibited the nuclease activity of CAD, while no inhibitory effects were observed in GST-CIA-ΔN and GST-CIA-CEN. Based on the results, it can be suggested that CIA interacts directly with CAD through its N-terminal region so as to inhibit the nuclease activity of CAD.

<7-2> Inhibitory Effect of CIA on DNA Fragmentation

In order to examine the inhibitory effect of CIA on DNA fragmentation in mammalian cells, an HA-tagged CIA clone or its deletion mutants were co-transfected, together with CAD-Flag or ICADL, into 293 cell lines in the presence or absence of caspase-3. After culturing of the transformed cells for 48 hours, genomic DNA was extracted from each cell and electrophoresed on a 2% agarose gel.

Figure 11:
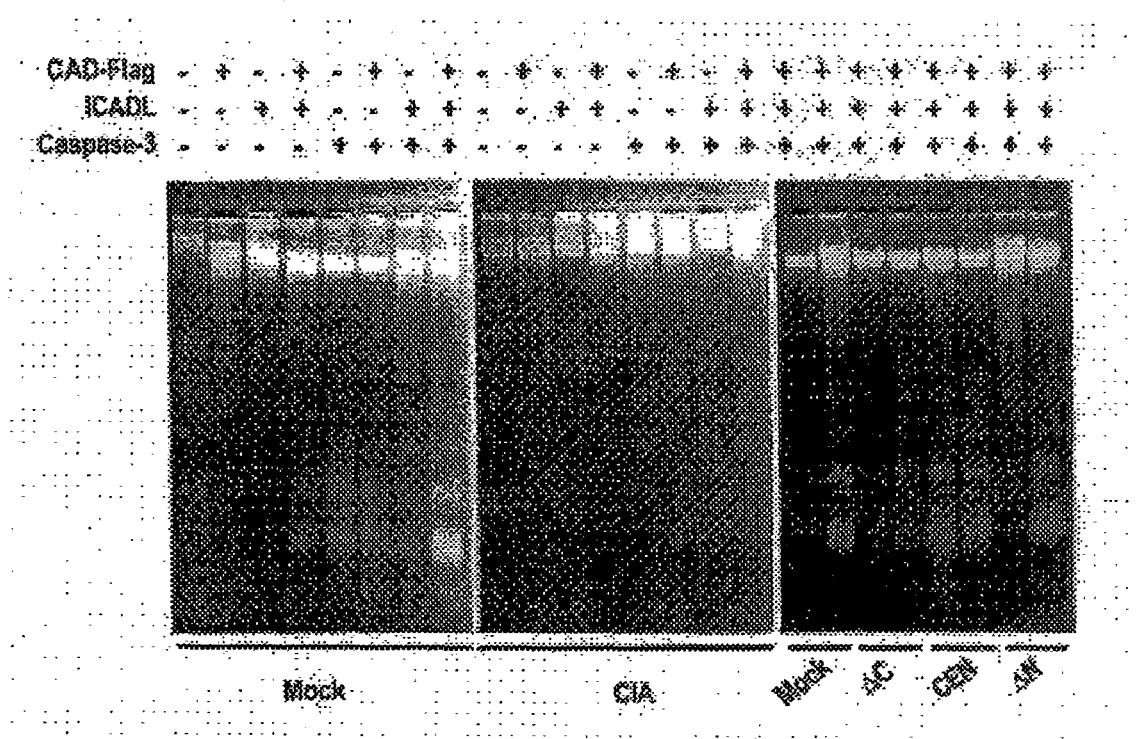
FIG. 11 is photographs showing the results of electrophoresis identifying the inhibitory activity of CIA against DNA fragmentation mediated by caspase-3 in 293 cell line.

The electrophoresis results visualized with ethidium bromide are given in FIG. 11. As seen, the super-expression of CAD/ICADL and caspase-3 in the cells that did not harbor the HA-CIA clone induced apparent DNA fragmentation, whereas the expression of HA-CIA inhibited CAD/ICADL and caspase-3 from inducing DNA fragmentation. In the case of the cells transformed with deletion mutants of CIA, the DNA fragmentation of CAD was found to be inhibited by the mutants HA-CIA-ΔC and HA-CIA-CEN, both containing the N-terminal region responsible for the direct interaction with CAD as seen in immunoblots of FIG. 12.

Accordingly, it can be concluded that CIA is a CAD inhibitor whose inhibitory activity against the nuclease activity and DNA fragmentation by CAD is performed by the direct interaction between its N-terminal region and CAD.

Example 8

Apoptosis and DNA Fragmentation in 293-CIA Cells

In this example, the research focus was turned from CIA's function as a CAD inhibitor in vitro to inhibit CAD-mediated apoptosis and DNA fragmentation to CIA'S function as an anti-apoptotic regulator in vivo.

<8-1> Transfection of CIA into 293 Cell Line

CIA clones were transfected into 293 cell line. First, 293-cells, derived from human embryonic kidney cells, were inoculated in DMEM (Dulbeco's modified Eagle's medium containing 100 U/ml penicillin/streptomycin, Gibco BRL), supplemented with 10% heat-inactivated fetal bovine serum, followed by culturing the cells at 37° C. in a 5% CO$_2$ humidified atmosphere. HA-CIA was introduced into the cells by electroporation. To this end, cells were suspended at 1×10$^7$ cells/plate in 500 μl of HEPES and added with an appropriate amount of HA-CIA DNA. To the solution, electric pulses were applied by using Gene Pluser II (BioRad Inc. USA) according to the manufacture's instruction, after which the cells that expressed HA-CIA were selected in the presence of G418. Immunoblotting analysis was performed using an anti-HA monoclonal antibody to examine the expression of HA-CIA.

Figure 12:
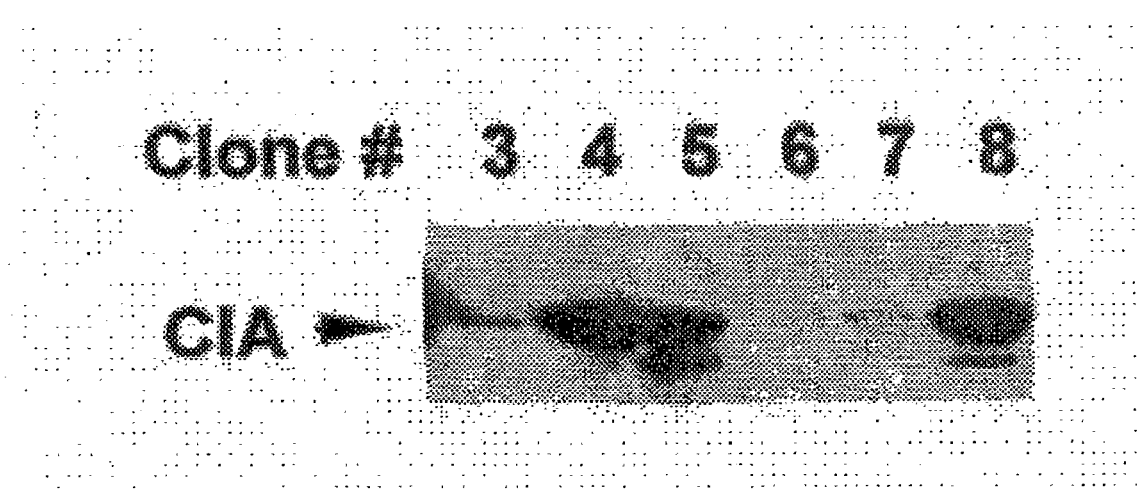
FIG. 12 is a photograph showing the result of immunoblot identifying the stable expression of ectopic CIA in 293 cells.

As shown in immunoblots of FIG. 12, HA-tagged CIA was stably expressed in 293-cells, which are low in the endogenous expression level of CIA. For use in the following experiments, clones #4 and #6 that showed the highest and the lowest CIA expression levels, respectively, were selected.

<8-2> Resistance of 293-CIA cell to Stress-Caused Apoptosis

An examination was made of the influence of CIA on stress-induced apoptosis. 293-cells, 293-CIA#4 cells and 293-CIA#6 cells were treated with a mixture of 10 μg/ml cycloheximide and 20 ng/ml TNF (TNF/CHX) or with 1 μM staurosporine (STS) or irradiated with UV light at an intensity of 80 J/m$^2$ to cause apoptosis. After 6, 12 or 24 hours of culturing, the cells were treated with 70% ethanol for 1 hour in ice for fixation. The fixed cells were dyed with 50 μg/ml popidium iodide (PI), followed by FACS (FacsCalibur, Becton-Dickinson) analysis for hypoploid cell fractions.

Figure 13:
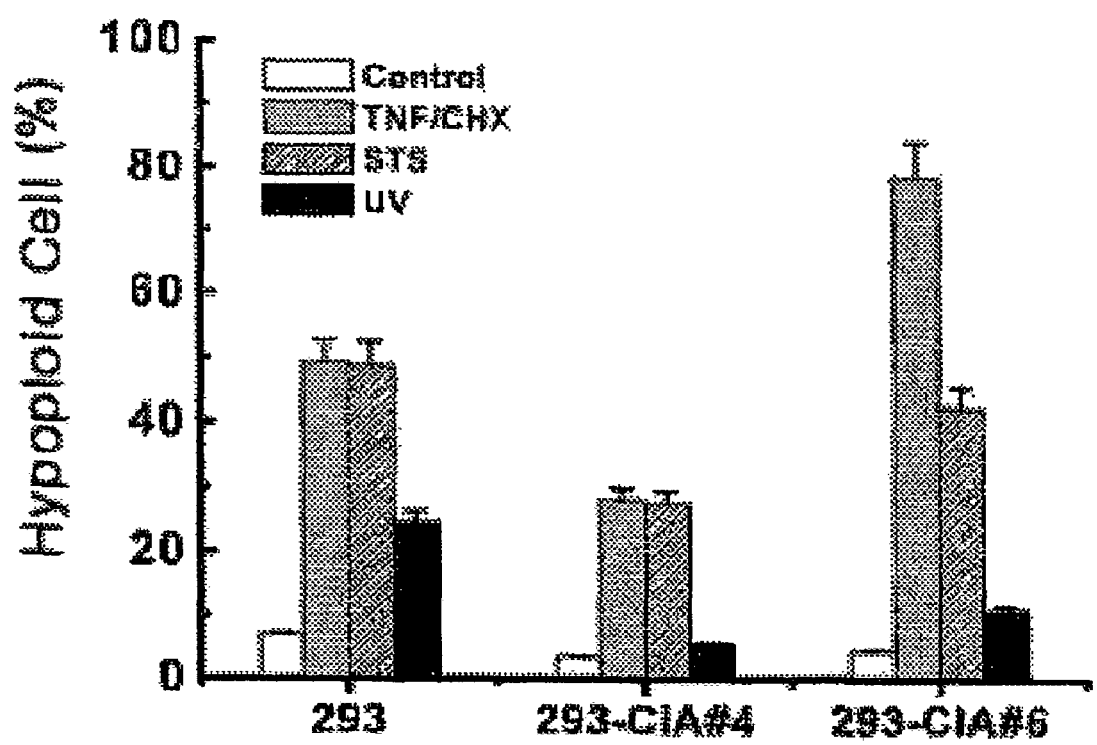
FIG. 13 is a graph showing the resistance of CIA-expresing 293 cells to stress-induced apoptosis.

The FACS analysis results are given in FIG. 13. 293-cells and 293-CIA#6 cells, both being low in CIA expression level, showed about 5–8 fold larger hypoploid cell fractions due to the apoptosis caused by TNF/CHX, STS or UV light than did control cells. In contrast, significant reductions were observed in percentages of 293-CIA#4 cell's hypoploid cell fractions because CIA was expressed to inhibit the apoptosis caused by the stimuli. Accordingly, cells transfected with the CIA of the present invention are resistant to stress-caused apoptosis.

<8-3> Resistance of 293-CIA Cells to ASK1-Mediated Apoptosis

It was revealed in Example 4-3 that CIA inhibits the kinase activity of ASK1 to inactivate the ASK1-mediated JNK/SAPK pathway, resulting in suppression of cell death and DNA fragmentation. In order to examine whether CIA inhibits ASK1-mediated apoptosis in vivo, expression vectors pcDNA3-Daxx (498–740) (granted from Dr. Sung-Hoon, Kim, Sungkyunkwan Univ. Korea), pCMV2-Flag-ΔMEKK1 (granted from Michael Karin, UCSD), or pcDNA3-ASK1ΔN-Flag (constructed by cloning into the EcoRI/XbaI restriction site of pcDNA3-Flag an ASK1 fragment obtained through PCR) was transiently transfected into 293 or 293-CIA#4 cells. After being cultured for 48 hours, the transformants were treated with 70% ethanol in ice for fixation. The fixed cells were dyed with 50 μg/ml of PI for FACS analysis for hypoploid cell fractions.

Figure 14:
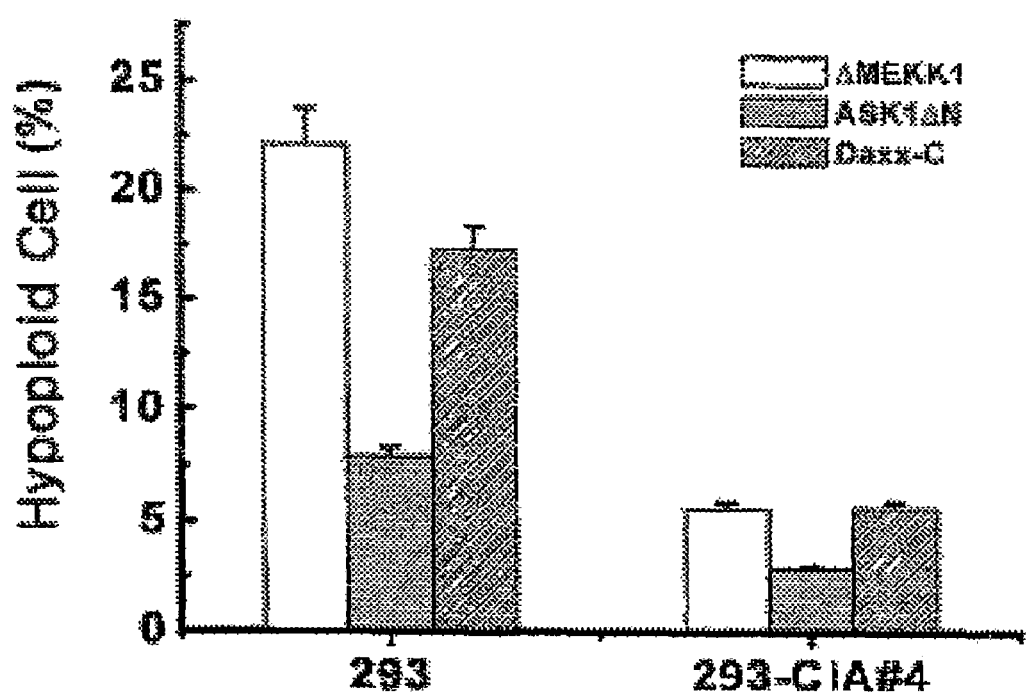
FIG. 14 is a graph showing the resistance of CIA-expressing 293 cells to ASK1-mediated apoptosis.

The FACS analysis results are given in FIG. 14. A large hypoploid cell fraction was detected in the 293-cells transformed with the expression vector containing Daxx because the superexpression of Daxx activates ASK1-mediated apoptosis. On the contrary, 293-CIA#4 cells showed relatively low hypoploid cell fractions because the co-expressed CIA blocked the JNK/SAPK pathway activated by Daxx. These results, taken together, indicate that CIA can inhibit CAD-mediated DNA fragmentation as well as apoptosis by suppressing the activity of ASK1 and its downstream JNK/SAPK pathway.

INDUSTRIAL APPLICABILITY

As shown above, the novel CIA gene or its protein of the present invention functions as a selective inhibitor of CAD- and ASK1-mediated apoptosis. Based on its intracellular functions, the CIA gene or protein can be used as a therapeutic agent for treatment of degenerative diseases of the cranial nervous system, apoplexy, cancer, diseases of immunologic system and inflammation.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An inhibitor of ASK1 (apoptosis signal-regulating kinase 1) or CAD (caspase-activated deoxyribonuclease) containing a mouse CIA (CAD inhibitor interacting with ASK1) protein having the amino acid sequence of SEQ ID NO: 4.

2. A therapeutic agent for treatment of apoptosis-related diseases containing a mouse CIA (CAD inhibitor interacting with ASK1) protein having the amino acid sequence of SEQ ID No: 4.

3. The therapeutic agent for treatment as set forth in claim 2, wherein the apoprosis-related diseases are degenerative diseases of the cranial nervous system, apoplexy, cancer, immune disorders or inflammation.

4. A method for inhibiting apoprosis of mammalian cells, comprising the step of introducing an amount of the CIA (CAD inhibitor interacting with ASK1) protein of SEQ ID No: 4 into a mammalian cell sufficient to inhibit apoptosis.

5. A method for inhibiting ASK1 (apoptosis signal-regulating kinase 1) activity, comprising the step of introducing an amount of CIA protein of SEQ ID No: 4 into a mammalian cell sufficient to inhibit ASK1 activity.

6. A method for inhibit CAD (caspase-activated deoxyribonuclease) activity, comprising the step of introducing an amount of CIA protein of SEQ ID No: 4 into a mammalian cell sufficient to inhibit CAD hactivity.

* * * * *